(12) United States Patent
Ramm et al.

(10) Patent No.: US 9,057,701 B2
(45) Date of Patent: Jun. 16, 2015

(54) SYSTEM AND METHODS FOR RAPID AND AUTOMATED SCREENING OF CELLS

(75) Inventors: Peter Ramm, St. Catharines (CA); Yuriy Alexandrov, Cardiff (GB); Jurich Cybuch, St. Catharines (CA); Paul Donders, Ontario (CA); Carlos Zarate, Caba (AR); Bohdan J. Soltys, Oakville (CA)

(73) Assignee: GE HEALTHCARE NIAGARA INC., Mississauga, Ontario (CA)

( * ) Notice: Subject to any disclaimer, the term of this patent is extended or adjusted under 35 U.S.C. 154(b) by 925 days.

(21) Appl. No.: 12/817,422

(22) Filed: Jun. 17, 2010
(Under 37 CFR 1.47)

(65) Prior Publication Data
US 2010/0254590 A1 Oct. 7, 2010

Related U.S. Application Data

(63) Continuation of application No. 12/253,275, filed on Oct. 17, 2008, now Pat. No. 7,764,822, which is a continuation of application No. 10/514,925, filed as application No. PCT/IB03/01821 on May 9, 2003, now Pat. No. 7,469,056.

(60) Provisional application No. 60/380,822, filed on May 14, 2002.

(51) Int. Cl.
*G06K 9/00* (2006.01)
*G01N 21/64* (2006.01)
(Continued)

(52) U.S. Cl.
CPC ........ *G01N 21/6458* (2013.01); *G01N 15/1475* (2013.01); *G01N 21/6428* (2013.01); *G01N 33/5026* (2013.01); *G01N 2015/1497* (2013.01); *G01N 2333/4603* (2013.01); *G06K 9/00127* (2013.01); *G06T 7/0012* (2013.01); *G06T 2207/10056* (2013.01); *G06T 2207/20141* (2013.01); *G06T 2207/30024* (2013.01)

(58) Field of Classification Search
USPC ................................ 382/128–133; 435/5, 71
See application file for complete search history.

(56) References Cited

U.S. PATENT DOCUMENTS

| 4,881,808 A | 11/1989 | Bille et al. |
| 5,018,209 A | 5/1991 | Bacus |

(Continued)

FOREIGN PATENT DOCUMENTS

| WO | WO 92/15034 | 9/1992 |
| WO | WO 95/22058 | 8/1995 |

(Continued)

*Primary Examiner* — Amara Abdi

(57) ABSTRACT

A system for performing automated cell screening in drug discovery, includes an automated microscope, a fast autofocus device, and a digital imaging system. Processes are implemented in software through which relevant cellular material is segmented and quantified with minimal user interaction. Improvements in the following areas: known methods for image processing are implemented in such a way that automated segmentation is achieved; sets of known measurements (pixel counting, etc.) are implemented as methods which demonstrate aspects of biology in a reliable fashion; components for automated positioning, focusing, imaging and processing of a multiplicity of samples are integrated as systems within which the segmentation and measurement methods may be mounted; and components and methods are adapted into systems which yield more highly automated and more rapid cell screening.

8 Claims, 28 Drawing Sheets

(51) Int. Cl.
*G01N 15/14* (2006.01)
*G01N 33/50* (2006.01)
*G06T 7/00* (2006.01)

(56) References Cited

U.S. PATENT DOCUMENTS

| | | |
|---|---|---|
| 5,072,382 A | 12/1991 | Kamentsky |
| 5,281,517 A | 1/1994 | Bacus et al. |
| 5,287,272 A | 2/1994 | Rutenberg et al. |
| 5,627,908 A | 5/1997 | Lee et al. |
| 5,741,648 A | 4/1998 | Hemstreet, III et al. |
| 5,856,665 A | 1/1999 | Price et al. |
| 5,932,872 A | 8/1999 | Price |
| 5,978,498 A | 11/1999 | Wilhelm et al. |
| 5,989,835 A | 11/1999 | Dunlay et al. |
| 6,103,479 A | 8/2000 | Taylor |
| 6,130,745 A | 10/2000 | Manian et al. |
| 6,252,979 B1 | 6/2001 | Lee et al. |
| 6,271,036 B1 | 8/2001 | Hewitt et al. |
| 6,307,957 B1 | 10/2001 | Gutkowicz-Krusin et al. |
| 6,718,053 B1 | 4/2004 | Ellis et al. |
| 6,876,760 B1 * | 4/2005 | Vaisberg et al. ............... 382/129 |
| 6,986,993 B1 * | 1/2006 | Ghosh et al. .................. 435/7.1 |
| 2001/0028510 A1 | 10/2001 | Ramm et al. |

FOREIGN PATENT DOCUMENTS

| | | |
|---|---|---|
| WO | WO 98/44375 | 10/1998 |
| WO | WO 00/37984 | 6/2000 |
| WO | WO 01/11340 | 2/2001 |

* cited by examiner

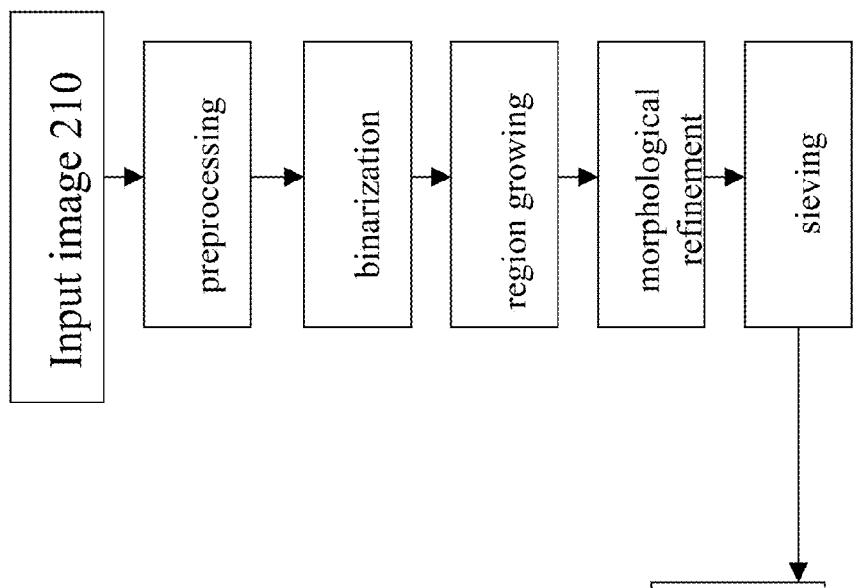
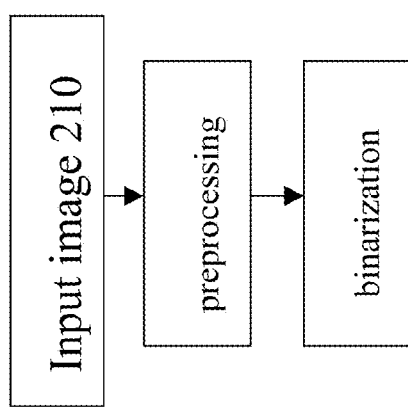
Fig. 11

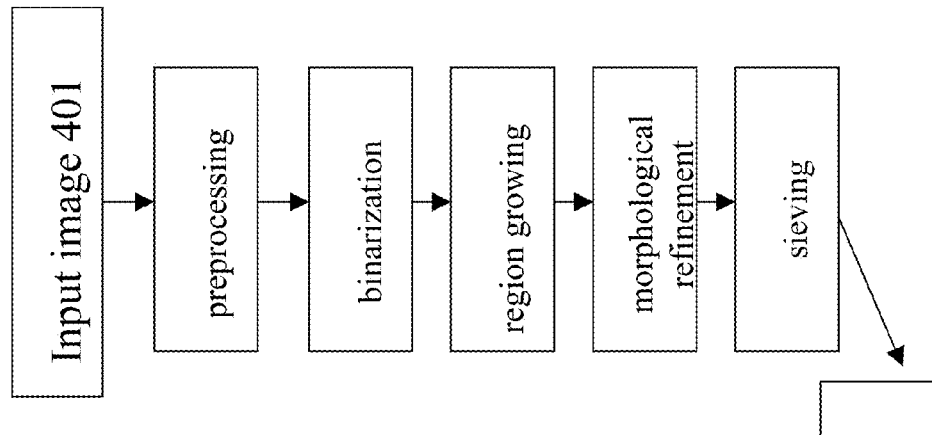
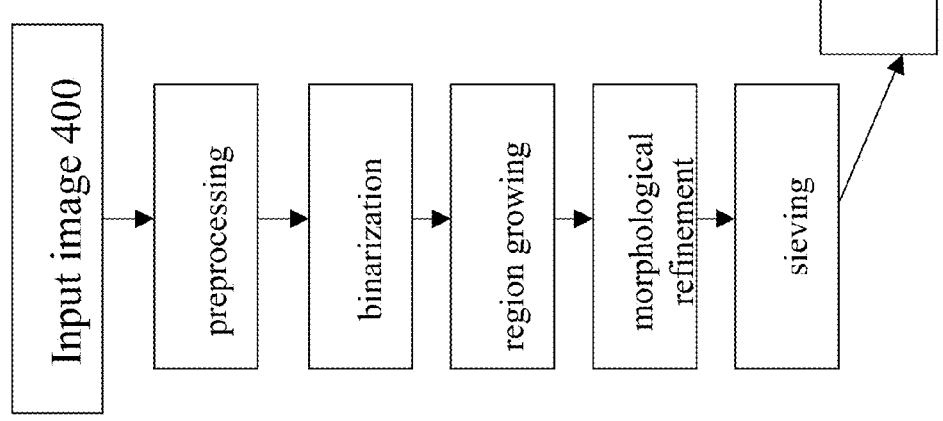
Fig. 23

SYSTEM AND METHODS FOR RAPID AND AUTOMATED SCREENING OF CELLS

CROSS-REFERENCE TO RELATED APPLICATIONS

This application is a continuation of U.S. patent application Ser. No. 12/253,275 filed Oct. 17, 2008, which is a continuation of U.S. patent application Ser. No. 10/514,925 filed Nov. 12, 2004, now U.S. Pat. No. 7,469,056, which is a filing under 35 U.S.C. §371 and claims priority to international patent application number PCT/IB2003/001821 filed May 9, 2003, which claims priority to U.S. provisional patent application No. 60/380,822 filed May 14, 2002.

FIELD OF THE INVENTION

The present invention relates generally to automated cell screening in drug discovery and, more particularly, concerns a system for performing such screening, including an automated microscope, a fast autofocus device, and a digital imaging system; as well as processes implemented in software through which relevant cellular material is segmented and quantified with minimal user interaction.

BACKGROUND OF THE INVENTION

New drug candidates are discovered by testing compounds against targets, a process termed screening. Traditionally, screening was a relatively slow process, with major pharmaceutical companies able to screen hundreds or a few thousands of compounds per week. This was acceptable, because the available compounds and biological targets were quite limited in number.

Recent advances in compound synthesis (e.g. combinatorial chemistry) and in the identification of biological targets (from genomics, proteomics and other disciplines) have led to a change in the nature of screening. There are many more compounds and the number of targets is also projected to grow rapidly. The extent of the growth can be appreciated if one considers that current drugs target about 450 of the estimated 50,000 potential gene products, each of which is a possible target. This is to say nothing of the targets that will be made available from the study of gene products (proteins). Therefore, the number of tests that could be done has become very large and will continue to grow. Pharmaceutical screening departments are implementing technologies which promise to increase the rate of testing. Their logic is that the more tests conducted per unit of time, the more often a new drug candidate will be discovered.

Screening at high rates is termed "high throughput screening" (HTS), and may be defined as the process of making thousands or many thousands of tests per day. HTS requires instruments and robotics optimized for high throughput, and systems for this purpose have been disclosed (e.g. US published patent application No. 2001/0028510 to Ramm et al.).

Most commonly, the instruments and robotics used for HTS do not accommodate tissues. Rather, they are applied to compounds and isolated targets. A compound of interest (referred to as the compound) is tested against a target (another compound, receptor molecule, protein or other), using label incorporation or some other property to reflect molecular interactions between the compound and its target. High throughput testing of compounds against targets is termed "primary screening." Given that primary screening makes many thousands of tests per day, and that a proportion of those tests yields compounds worthy of further investigation ("hits", usually less than 0.5% of the screen), hits generated by primary screening are accumulating at an unprecedented rate. These hits must be evaluated in post-primary screening stages, to characterize the efficacy, toxicity and specificity of the hit compounds. With these factors characterized, a small number of the best-qualified hits ("leads") can be moved into very costly and time-consuming pre-clinical and clinical trials.

Unfortunately, post-primary testing is more complex and much slower than primary testing. It is not enough to simply detect molecular interactions between compounds and isolated target molecules. Rather, compounds must be tested for interaction with tissues. Therefore, the accumulation of hits is now a major bottleneck within the drug discovery pipeline and there is a need for post-primary tests which can verify leads at rates higher than possible in the past.

The bottleneck can be mitigated if post-primary tests are efficient in demonstrating interactions of compounds with biology. One promising path is to perform post-primary assays upon cells. Cells can provide a more biologically relevant test than is obtained from a simple compound mixture. At the same time, cell assays are less costly, much quicker to conduct and more socially acceptable than assays conducted in complex organisms (e.g. rodents). It is projected that the importance of cell-based assays will continue to grow, as cellular models for ogranismic response continue to develop and improve.

A potential problem with cell assays is the relatively low level of throughput that most evidence. For example, a "metabolic rate" method is disclosed by Dawes (1972), and a "pooled quantity" method described in Freshney (1987). These types of low throughput techniques are typical of those used to analyze cell populations without the use of imaging or other high throughput methods of detection.

To achieve higher rates of throughput, image-based measurements may be made upon cell populations (e.g. Malay et al., 1989; Schroeder and Neagle, 1996; Ramm, 1999), and may be combined with various methods for automating and optimizing the processes of handling, imaging, and analyzing the cellular samples. In these disclosures, the entity of measurement is a population of cells within each of a plurality of wells in a microwell plate. Cellular or subcellular detail is not resolved.

Detection of cell population responses may be contrasted with a requirement for detection of effects occurring within discrete cells in a population. In this case, cellular or subcellular resolution is required and a number of systems and methods for microscopic cell screening have been developed. As with population screens, the key is to construct systems and methods which automate and optimize the processes of handling, imaging, and analyzing the cellular samples. With the present invention, automated cell screens can be conducted with single cell and subcellular resolution.

Image Cytometry

"Cytometry" is the measurement of features from discrete cells. "Image cytometry" is the use of imaging systems to perform cytometric measurements. Cytometric measurements may or may not require subcellular detail. If discrete cells are imaged at low resolution, each cell occupies a small number of image pixels and is treated as a homogenous measurement point (e.g. Miraglia et al., 1999). We refer to these as "point cell assays." Cellular anatomy can also be resolved at higher resolution, with parts of cells each occupying numbers of pixels. The level of subcellular resolution ranges from the visualization of only the largest structures (e.g. Galbraith et al., 1991), to the resolving of subcellular organelles (most of the material dealt with in this body of art). Common classes of cytometric measurement include:

Morphometry—the size, shape, and texture of cells, nuclei and organelles. For example:

Neurite outgrowth is used as an index of neural development or regeneration (Masseroli et al., 1993; Siklos et al, 1993; Malgrange et al, 1994; Mezin et al, 1994; Turner et al, 1994; de Medinaceli et al, 1995; Pauwels et al, 1995; Ventimiglia et al, 1995; Stahlhut et al, 1997; Isaacs et al, 1998; Bitsland et al, 1999; Pollack et al, 1999; Ronn et al, 2000).

Changes in nuclear size, shape and chromatin distribution can be correlated with progression through the cell cycle. (e.g. De Le Torre and Navarrete, 1974; Sawicki, et al., 1974; Giroud, 1982), or with classification of proliferative tendencies (e.g. Crissman et al., 1990; Martin et al., 1984; Smith et al., 1989; Souchier et al., 1995).

Morphometry is commonly implemented upon diagnostic imaging cytometers. These are automated devices, which incorporate dedicated components and software methods for clinical screening (e.g. as disclosed in Lee et al., 1992; Wied et al., 1987; U.S. Pat. Nos. 5,281,517; 5,287,272; 5,627,908; 5,741,648; 5,978,498; 6,271,036; 6,252,979).

Functional analysis—It is common to measure the amount of a substance or comparative amounts of a substance or substances within subcellular compartments, and to use that measurement as an index of cellular function.

Ion channels Changes in cellular electrical potential reflect the operation of ion channels. Intracellular label localization can be used as an alternative to electrophysiology, to investigate the operation of ion channels (e.g. review in Taylor et al., 2001; Omalley, 1994).).

Translocation (movement of proteins between subcellular compartments) Proteins are localized in two types of subcellular compartments. They may be embedded in or associated with membranes (e.g. receptors decorating a cell membrane), or they may be in an aqueous phase (in nucleoplasm or cytoplasm). Many cellular functions are associated with protein transitions between these compartments. Functional imaging can be used to examine localization to specific intracellular receptor compartments (e.g. Luby-Phelps et al., 1985) or trafficking of receptors between cellular compartments. For example, Georget et al. (1998) and Trapman and Brinkmann (1993) disclose the analysis of receptor localization using imaging quantification of the nuclear/cytoplasmic ratio. A fluor labels the receptor, and movement of the fluor reflects alteration in the location of receptor molecules between nucleus and cytoplasm.

Localization (amount of protein within a cellular or subcellular compartment) Abundance of any (e.g. structural) proteins in subcellular compartments (e.g. nucleus and cytoplasm) can be used as an index of function (e.g. of proliferative tendency as in Kawamoto et al., 1997).

Cytometric systems for morphometry and functional analysis may be built around image analyzers of the type marketed by many commercial entities. Some such systems are designed for application in research labs (research systems), and require frequent operator interaction to perform their function. Therefore, these systems investigate a small number of specimens in a given time period. An example of such a system is the MCID image analyzer from Imaging Research Inc. Other such systems are designed for application in industrial drug discovery (industrial systems) or cell diagnostics (diagnostic systems), and they function without frequent operator interaction (automated), and investigate a relatively large number of specimens in a given period (termed "high throughput"). Examples of industrial high throughput systems are the AutoLead Cell Analyzer from Imaging Research Inc. and the ArrayScan II from Cellomics Inc. An example of a cell diagnostic system is the LSC from CompuCyte Inc.

Numerous publications generated with research systems describe methods for making morphometric and functional measurements upon cells. Widely known examples of such measurements include ratios of size or label intensity between nucleus and cytoplasm, or the relative intensity of fluorescence (as generated by standard fluorescence methods or spatially dependent methods such as fluorescence resonance energy transfer), emitted at multiple wavelengths.

Research systems have a theoretical application to diagnosis and screening, in that they can be programmed and operated to implement any cell detection method (e.g. Serra, 1982 is often cited). Most industrial and diagnostic systems use known image processing methods which have also been implemented on research systems to enhance the detection of cells in images.

However, research systems lack the automation and throughput which would make them useful for industrial drug discovery or clinical diagnosis. Most commonly, an operator must interact with the system on a frequent basis. For example, Bacus (U.S. Pat. No. 5,018,209) discloses one such operator-assisted diagnostic system, which is useful with small numbers of samples, but which would not be useful in a high throughput environment.

Methods Employed in Cytometric Imaging Systems
Presegmentation

It is common to preprocess images to enhance the detectability of features. For example, certain convolution filters such as the Prewitt (O'Gorman et al., 1985) and Hueckel (Hueckel, 1971) can sometimes better demonstrate a cell periphery than unfiltered images. Such methods improve the accuracy of subsequent segmentation and can result in a reduced requirement for operator editing of segmented pixels.

Other widely known corrections are applied to correct inhomegenities within the collection optics and illumination field, and to correct local (e.g. as disclosed in U.S. Pat. No. 5,072,382) or global (as commonly applied in many commercial imaging systems) background variations. In this respect, it is common to acquire an image of a blank field, process the image in some way to remove high frequency intensity variations, calculate a deviation from a reference pixel value at each location in the processed image, and save the matrix of deviation factors as a correction matrix (e.g. as reduced to practice in the MCID system from Imaging Research). The correction matrix is used to improve the homogeneity of the background in subsequent images.

Segmentation

Before a measurement may be made, relevant image features must be discriminated from background. This discrimination is performed using widely known methods for image segmentation (reduced to practice in many commercial products, e.g. the ImagePro software from Media Cybernetics). Segmentation is defined as the process that subdivides an image into its constituent parts or objects. Tracing and thresholding are known methods for segmentation (there are others). Ideally, a simple staining process yields unambiguous detection of cells or cellular components, wherein each stained object marks a feature of interest, and other image components are unstained. The goal is that the objects are bright or dark enough to be detected with a simple intensity criterion. In practice, this goal is rarely achieved.

Tracing

The simplest manual segmentation method is for the human operator to trace cells and subcellular detail. The system then uses pixels within the trace to report parameters of interest (e.g. Deligdisch et al., 1993; Gil et al., 1986).

Thresholding

The simplest automated segmentation method, intensity thresholding, takes a grayscale or color image as input, histograms the intensity frequencies, and outputs a binary image based on a single discriminating value (the threshold). Simple intensity or color thresholding is rarely adequate for industrial applications in that only some of the segmented pixels are valid and the segmented image needs operator editing. For example, Takamatsu et al. (1986) report that simple intensity thresholding resulted in lower precision for cell detection than was attained by flow cytometry. There are many problems, including cell and background intensities that vary from location to location in a single image or set of images.

Target Regions

Once image pixels are segmented as being of possible relevance, they must be classified as fitting within features of interest (termed regions or targets). The point is to group pixels to distinct regions according to criteria of homogeneity. Homogeneity criteria are based on some parameter (e.g. distance separating detected pixels), which can be derived in a variety of known ways. Among techniques for region extraction, the least complex method involves manual or semi-automated extraction. In this process people confirm or identify the assignment of segmented pixels to regions.

"Region growing" is the process of amalgamating separated segmented pixels into regions. There are many criteria that can be used for region growing (e.g. Chassery and Garbay, 1984; Garbay 1986; Ong et al., 1993; Smeulders et al. 1979). For example, geometric features (e.g. distance from another region, size, shape, texture, frequency distribution, fractal dimensions, local curvature) or statistical features (e.g. variance, mode, skewness, kurtosis, entropy) could be used as part of the classification of pixels to regions. Region growing can also be based on morphological techniques. For example, Seniuk et al., 1991 and U.S. Pat. No. 5,978,498 disclose the use of morphology in a series of steps using intensity-based masks to discriminate nuclear and cytoplasmic compartments, followed by erosion (to extract a clean nucleus) and dilation (to extract a clean cytoplasmic area).

Grown regions can then be passed to various higher level processes. For example, complex pixel statistics (e.g. multiscale wavelet maxima as disclosed in U.S. Pat. No. 6,307,957) can be applied to make measurements upon regions. Similarly, knowledge based methods for cellular classification take regions as input and make decisions as their output. These systems can incorporate expert systems and/or neural nets (e.g. U.S. Pat. No. 5,287,272; Refenes et al., 1990; Stotzka et al., 1995).

Cell Screening Systems

Research systems which use assemblages of known methods for measuring probe level within cells are widely disclosed (e.g. Macaulay and Palcic, 1990; Mize et al., 1988; Thompson et al., 1990; Zoli et al. 1990). Similarly, industrial cell screening systems implement known methods for presegmentation, segmentation, and target classification (e.g. as in the ArrayScan system from Cellomics and the InCell system from Amersham Biosciences). What distinguishes research and industrial systems from each other is that the industrial system will function with minimal operator interaction (automatically) and will provide higher rates of throughput. Research applications can be accomplished on almost any image analysis system. Automation and throughput can only be achieved within a system integrating specialized software and hardware.

As an example, a widely applied principle is that of marking a readily detected subcellular component, in order to improve subsequent detection of cell locations and of subcellular components adjacent to the marked component. Commonly, the marked component is a nucleus (e.g. as disclosed in Benveniste et al., 1989; Lockett et al., 1991; Anderson et al., 1992; Santisteban et al., 1992). In an industrial application (e.g. as disclosed in U.S. Pat. No. 5,989,835 and as supplied with the ArrayScan II from Cellomics, Inc.), cytoplasm around a marked nucleus can be defined (automatically) by an annulus so as to minimize intrusion of one cell cytoplasm upon another (the cytoplasm of which lies beyond the annulus). The same annulus method can be implemented on a research system, but without automation of the microscope system and software so as to operate with minimal user interaction and high throughput. Specifically, Seniuk et al. (1991) disclose a method for marking cell nuclei with a DNA-specific fluorescent probe, and then creating an annulus at a distance from the nucleus (in this case, 1 μm distance was used) for image-based measurements of cytoplasmic probe content.

Marking of cellular components and use of these components to localize other components are known methods. However, the assemblage of known methods into systems and methods usable in industrial cell screening systems constitutes novelty to the extent that these systems and methods yield better automation and throughput than is available in the prior art. The difficulty of creating such an automated and high throughput system is not to be underestimated, and is demonstrated by the very small number of such systems which have been disclosed or reduced to practice (e.g. Proffit et al., 1996; Ramm et al., 2001, 2002; U.S. Pat. No. 5,989,835; U.S. Pat. No. 6,103,479).

The present invention provides a system and process which achieve improvements in the following areas:

Presegmentation and segmentation Known methods for image processing are implemented in such a way that automated segmentation is achieved (e.g. as disclosed in Ramm et al., published U.S. patent application 2001/0028510).

Measurement Sets of known measurements (pixel counting, etc.) are implemented as methods which demonstrate aspects of biology in a reliable fashion (e.g. as disclosed in Ramm et al., 2001/0028510).

Optics, mechanicals and electronics Components for automated positioning, focusing, imaging and processing of a multiplicity of samples are integrated as systems within which the segmentation and measurement methods may be mounted.

COMPONENTS and methods are adapted into systems which yield more highly automated and more rapid cell screening.

In accordance with one aspect of the invention a library is provided of assay processing procedures that are structured into methods that perform automated analyses with minimal user interaction. Members of the library are:

Nonlinear suppression of high intensity peaks

Adaptive noise smoothing (Gaussian)

Adaptive noise smoothing and feature enhancement by nonlinear diffusion filtering Thresholding by optimal histogram bipartition Seeded region growing Texture transform Morphological refinement of detected features Quantification by local contrast
Distributional feature analyses
Frequency domain detection of granular details
Demarcation mapping
Background correction
Sieving Disclosed methods include neurite assays, granular translocation assays, nuclear translocation assays, and membrane ruffling assays.

In accordance with another aspect of the present invention, the methods are integrated within an automated opto-mechanical system that positions specimens located in a plurality of containers, focuses, and interfaces to laboratory automation equipment.

In accordance with a further aspect, the invention includes an electronic camera and computer, used to acquire and store images, and to host the software.

BRIEF DESCRIPTION OF THE DRAWINGS

The foregoing brief description, as well as further objects, features and advantages of the present invention will be understood more completely from the following detailed description of presently preferred, but nonetheless illustrative, embodiments in accordance with the present invention, with reference being had to the accompanying drawings, in which:

FIG. 11, on the left, shows a flow chart for the granule segmentation of the analysis of granular translocation assays;

FIG. 11, on the right, shows a flow chart for the cytoplasm segmentation of the analysis of granular translocation assays;

FIG. 23 is a flow chart illustrating the analysis of ruffle translocation;

DETAILED DESCRIPTION OF THE PREFERRED EMBODIMENTS

The denotations and abbreviations used in this description are defined in Table 1.

Figure 1:
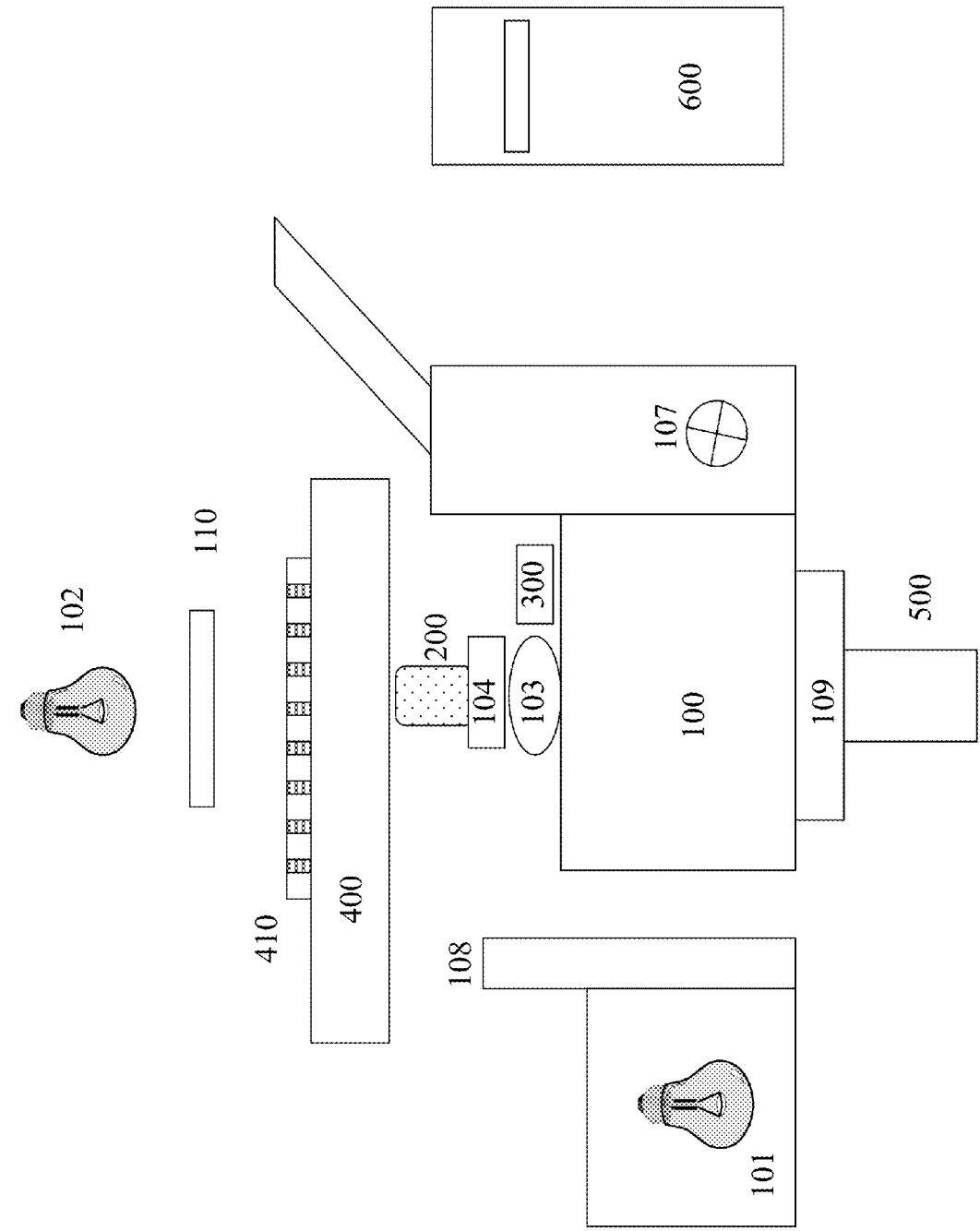
FIG. 1 is a schematic block diagram illustrating the optical, mechanical and electrical components of the system of the present invention.

Turning now to the details of the drawings, FIG. 1 is a schematic block diagram illustrating the optical, mechanical and electrical components of the system of the present invention. Inverted microscope stand 100 is equipped with fluorescence epi-illuminator 101 and tungsten halogen transilluminator 102. Mounted on objective turret 103 is fast motor drive 104, preferably of the piezoelectric kind. Motor 104 moves objective 200 in the Z-dimension (vertically) so as to reach the best focus position. The best focus position is defined by confocal autofocus device 300 as monitored by digital computer 600. Microscope Z-focus drive 107 may also be used to move objective 200 in the Z-dimension, when software autofocus is selected. Filter changer 108 is positioned so as to present filters in the illumination path of illuminator 101, thereby selecting narrow band excitation illumination. Optionally, filter changer 109 may be mounted in the emission path of microscope 100, so as to select narrow band emission optics under computer control. Shutter 110 transmits light from illuminator 102, under computer control. Motorized stage 400 carries multiwell plate 410 so as to present each of the plurality of wells to objective 200. CCD camera 500 is mounted so as to acquire images of cells in plate 410. Digital computer 600 controls the components (filter changers 108/109, shutter 110, focus components 104, 300, 107, stage 400, camera 500) and contains software to perform analyses.

The microscope 100 is, preferably, an inverted stand equipped with epifluorescence optics and with a transmitted light illumination path. The motorized and computer-controlled stage 400 is mounted on the microscope, so as to move specimen containers over the microscope optics. Preferably, the stage 400 is equipped with a holder for multi-well plates 410, and this holder is so constructed as to allow plate insertion and removal by standard laboratory robots such as the Twister 2 from Zymarc Industries. Digital camera 500, preferably a cooled and low-noise CCD camera, is mounted on the microscope so as to acquire specimen images. System control and image storage are performed by digital computer 600.

TABLE 1

List of Denotations and Abbreviations

| | |
|---|---|
| U(p) | Grayscale intensity of the grayscale image U at the location of pixel p |
| $\nabla$ | Symbol of linear differential vector operator "nabla" (Feynman 1964) |
| $\nabla_\sigma U$ | Gaussian gradient of image U (e.g. as explained in Jahne 1999, p. 241) |
| AND, OR etc. | Logical operations on binary images |
| A EXCP B | Composite logical operation defined as A XOR (A AND B). This operation has the meaning of exclusion from image A the common part of images A and B |
| Mean[U \| A] | Mean gray level value of the pixels within the subset A of the image U |
| Std[U \| A] | Standard deviation of the pixels within the subset A of the image U |
| N(A) | Number of elements in subset A (e.g. number of pixels within set of pixels A) |
| CSS | Cross-section size |
| MMS | Minimal morphological size |
| NDF | Nonlinear Diffusion Filtering |
| SGMD | Scalar "Gradient Modulus"-driven Diffusion |
| AEED | Anisotropic edge enhancing diffusion |
| ACED | Anisotropic coherence enhancing diffusion |
| SPED | Scalar peak enhancing diffusion |
| $\hat{D}$ | Diffusivity tensor |
| OHB | Optimal Histogram Bipartition |
| SRG | Seeded Region Growing |

Figure 2:
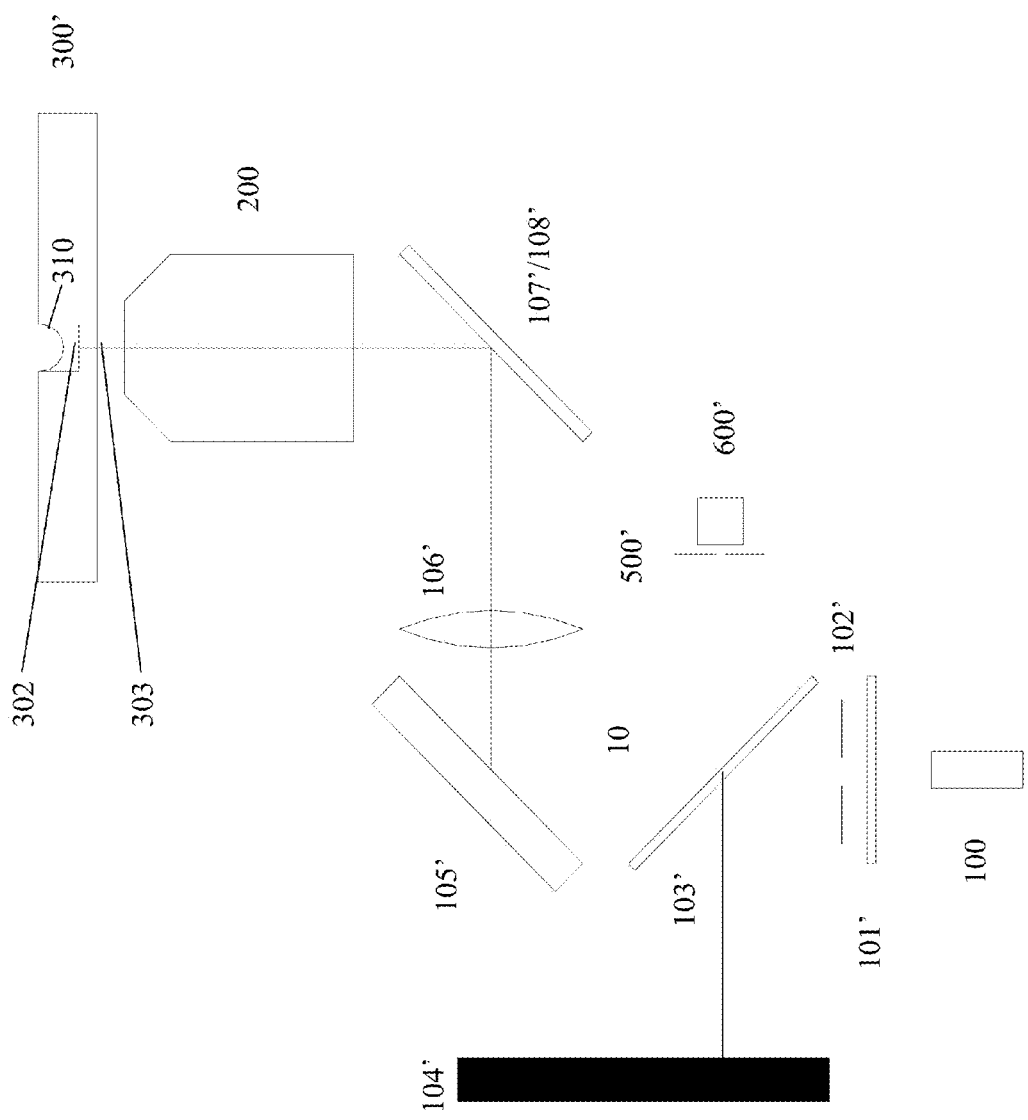
FIG. 2 is a schematic block diagram illustrating the fast autofocus device.

FIG. 2 is a schematic block diagram illustrating the fast autofocus device. Light emitted from a laser diode 100 passes through a transparent window 101', so calculated as to compensate for aberrations introduced by beam splitter 103'. This compensation is arrived at by tilting the window to introduce compensating aberrations. Should beamsplitter 103' be of a type that does not introduce aberrations (e.g. as in the case of a very thin beamsplitter), no correction from glass window 101' is required.

Leaving window 101', the laser beam then passes through an aperture 102' which limits the width of the beam so that it later fills the back lens of microscope objective 200. So as to operate with objectives with a back lens of 15-20 mm in diameter, the aperture is constructed with a diameter of 2.4 mm.

Beamsplitter 103' functions as a laser intensity limiting device. It is so constructed as to reflect >95% of the incident laser beam toward the side onto absorbing surface 104'. Preferentially, this absorbance is of a high order (close to 100%) so as to minimize retroreflections which could degrade measurement sensitivity by being incident to other components. The lateral reflection from beamsplitter 103' is so calculated as to diverge broadly as it proceeds towards absorbing surface 104' and there is minimal intrusion of focused reflections back towards detector 600'.

The system is designed so as to be efficient in the use of the remaining small proportion of the laser beam. The low power of the laser beam and the efficiency of the device allows the autofocus to be certified within a relatively non-restrictive category (Class 1). Were a larger proportion of the laser beam to be required for sensitive operation, the certification category would be more restrictive and both the cost and complexity of the device would be much greater.

Another light path is transmitted through beam splitter 103' so as to pass to mirror 105', which is of high flatness (λ/4) to maintain focus of the final beam, and of high reflectivity to maximize efficiency in the near infra-red and infra-red wavelengths that the laser emits. The mirror coating is of gold which has the property of efficiently reflecting the relevant wavelengths.

Light from mirror 105' is reflected to a positive lens 106' of such a focal length that it collimates the light and best fills the aperture of photodetector pin hole 500'. Preferably, lens 106' is diffraction limited with respect to the operating wavelength λ.

The collimated beam then passes to another mirror 107' which includes a filter 108'. An example of such a mirror is a high quality dichroic assembly with a flatness of λ/2, and with the property of transmitting wavelengths below 750 nm, and reflecting wavelengths above 750 nm. Mirror 107' is tilted at such an angle that it most efficiently reflects the desired wavelengths towards the back lens of objective 200. In a preferred embodiment, the back surface of mirror 107' is anti-reflection coated so as to minimize unwanted reflections.

Light is transmitted through microscope objective 200 to the bottom surface of a specimen container 300'. Objective 200 is moved in the vertical dimension relative to container 300', so as to sweep the laser beam through a detection volume which is thick enough to span a distance greater than the bottom surface of container 300' and which includes part of the contents of well 310.

Reflections from the interfaces between the transparent surfaces of container 300' and air (bottom surface 301) and fluid (inner surface 302) are collected by objective 200 and sent to filter/mirror 107'/108'. Mirror 107'/108' passes the laser wavelength preferentially and blocks other emissions from container 300' and specimen medium 303. The reflected light passes back through lens 106', mirror 105', and beam splitter 103', which directs part of the light back to photodetector 600'.

Photodetector 600' monitors the beam as objective 200 is moved to address sample volume 310. The amount of light produced by specular reflection can be calculated as:

$$I = (N-N')^2/(N+N')^2$$

Where N is the index of reflection of a first medium through which light passes, and N' is the index of reflection of a second medium through which light passes. The value of I is maximized when the refractive indices of N and N' are different.

Thus, a first transition 303 from air to the bottom of specimen container 310 will generate a larger reflection than a transition 302 from the material of the specimen container to a watery contained fluid. A software algorithm in computer 600 monitors the shape of the waveform produced by the photodetector in real time, and locates transition 302.

In operation, the positional autofocus of the present invention transmits a laser beam through the microscope objective and into the specimen container 300'. A rapid focus drive, which can be a piezo actuator, moves the microscope objective 200 in the z-plane (depth) relative to the plate bottom 301, establishing a sampling volume. At each point in the sampling volume, a retroreflection is transmitted to the confocal photodetector 600'. The photodetector monitors the reflection intensities, converting them to voltages which can be transmitted to the digital computer. Software in the computer calculates a best focus position on the basis of intensity characteristics arising as the illumination beam transits through surfaces of the specimen container. Components and construction of the device are similar to widely known embodiments of confocal optical paths (as disclosed in U.S. Pat. No. 4,881,808, U.S. Pat. No. 6,130,745, WO92/15034, WO95/22058, WO98/44375, WO00/37984). Some of these systems also detect a focus plane corresponding to a substrate upon which cells lie, and then establish a cell focus at some fixed distance beyond the substrate.

Figure 3:
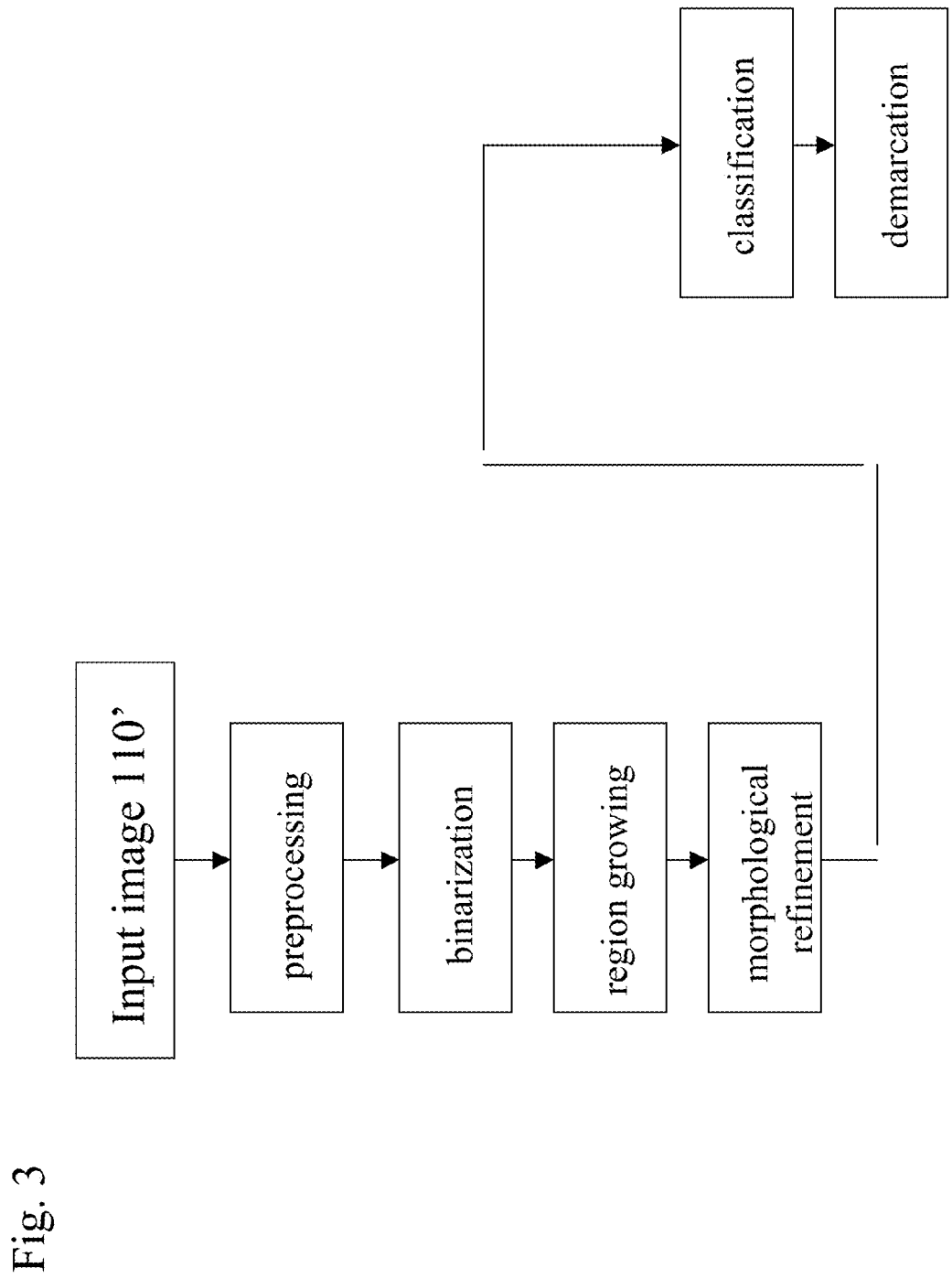
FIG. 3 is a flow chart, showing the general procedure for neurite analysis.

It is a feature of the autofocus of the present invention that it integrates a software autofocus algorithm so that it may be used with cells which lie at positions that are not fixed with respect to a surface of the container (e.g. within a range of 5-15 um above). The method involves these steps: a) use the best focus position achieved by the positional autofocus as a reference; b) move into the specimen container a fixed distance; c) take a number of images at intervals in the z-plane, and calculate a best focus from these images (FIG. 3). One skilled in the art will recognize that a software autofocus is slow when used alone, because it must take a large number of images. However, the use of the present hardware to come to a position defined by the specimen container, and then initiating a limited set of image acquisitions at a point referenced to that container allows the system of the present invention to function more rapidly than a software autofocus used alone.

It is a feature of the system of the present invention that it can also be used to focus thick specimens. For example, transient expression of green fluorescent protein (GFP) in dopaminergic neurons has been observed following injection of dopamine transporter promoter-GFP constructs into one-cell embryos of the zebrafish. These embryos are raised to adulthood to establish homozygous stocks of transgenic fish. Then, embryos of the transgenic line can be studied in a screening mode, by placing the embryos in microwell plates and administering compounds. These embryos are thicker than the depth of focus of a standard microscope objective. The system of the present invention accommodates specimens that extend beyond a single plane of focus. The method involves these steps: a) use the best focus position achieved by the positional autofocus as a reference; b) move into the specimen container a fixed distance; c) acquire a set of images in the z-plane, spanning a distance large enough to encompass the specimen; d) combine the images into a single image that best shows the entire thickness of the specimen using known image combination algorithms.

In another aspect, the same focus drive system can be used to create a stack of fluorescent Z-plane images from which a single best-focused image is calculated, using known methods for digital deconvolution. In this case, image deconvolution using known algorithms is substituted for image combination, as described above.

FIG. 3 is a flow chart, showing the general procedure for neurite analysis as further detailed in FIGS. 4-9. Original image 110' is subjected to a set of procedures which include image preprocessing, binarization, seeded region growing, morphological refinement, cell and neurite classification, and demarcation mapping.

Figure 4:
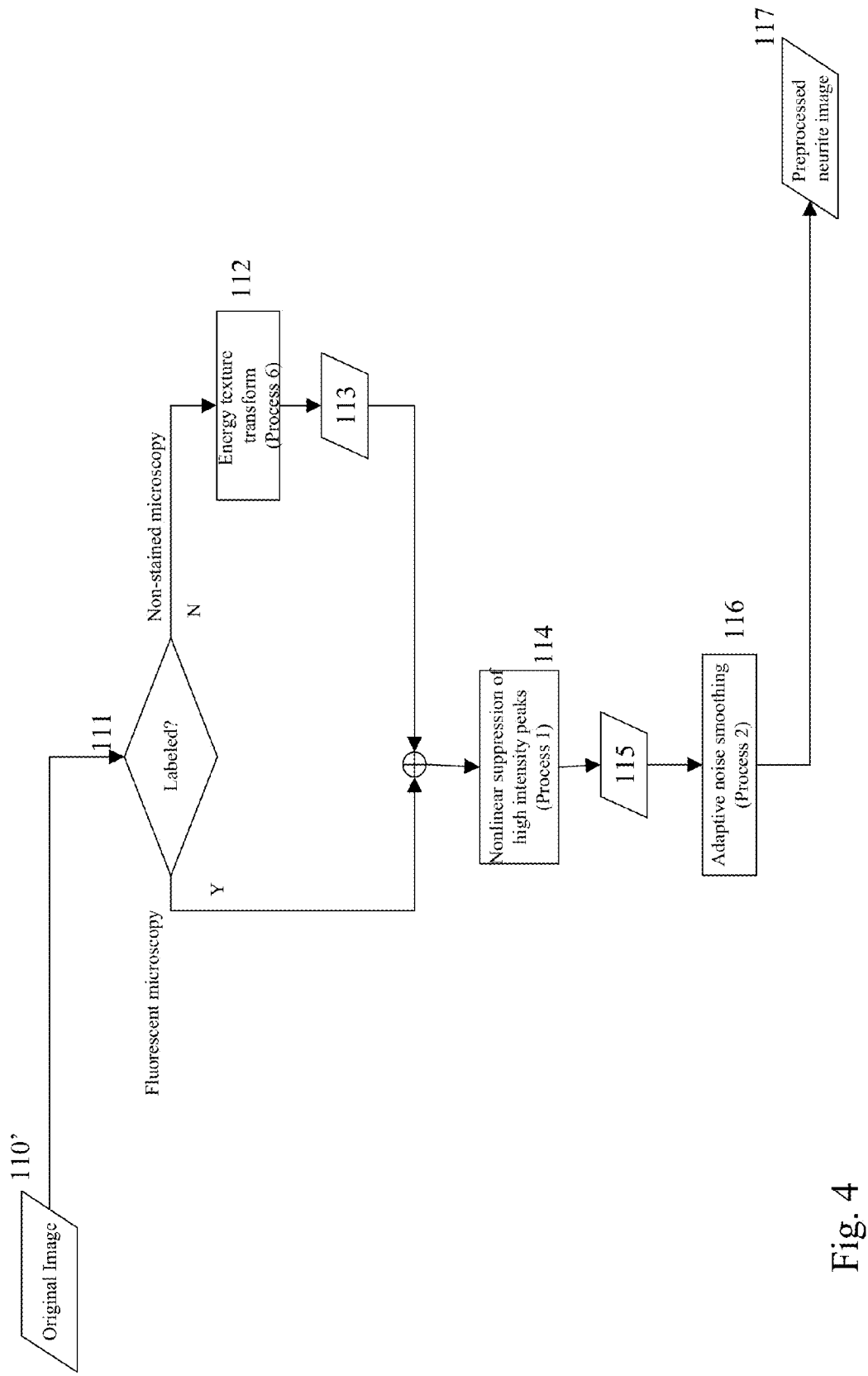
FIG. 4 is a flow chart showing the image preprocessing procedures used within the method for automated neurite analysis.
Figure 5:
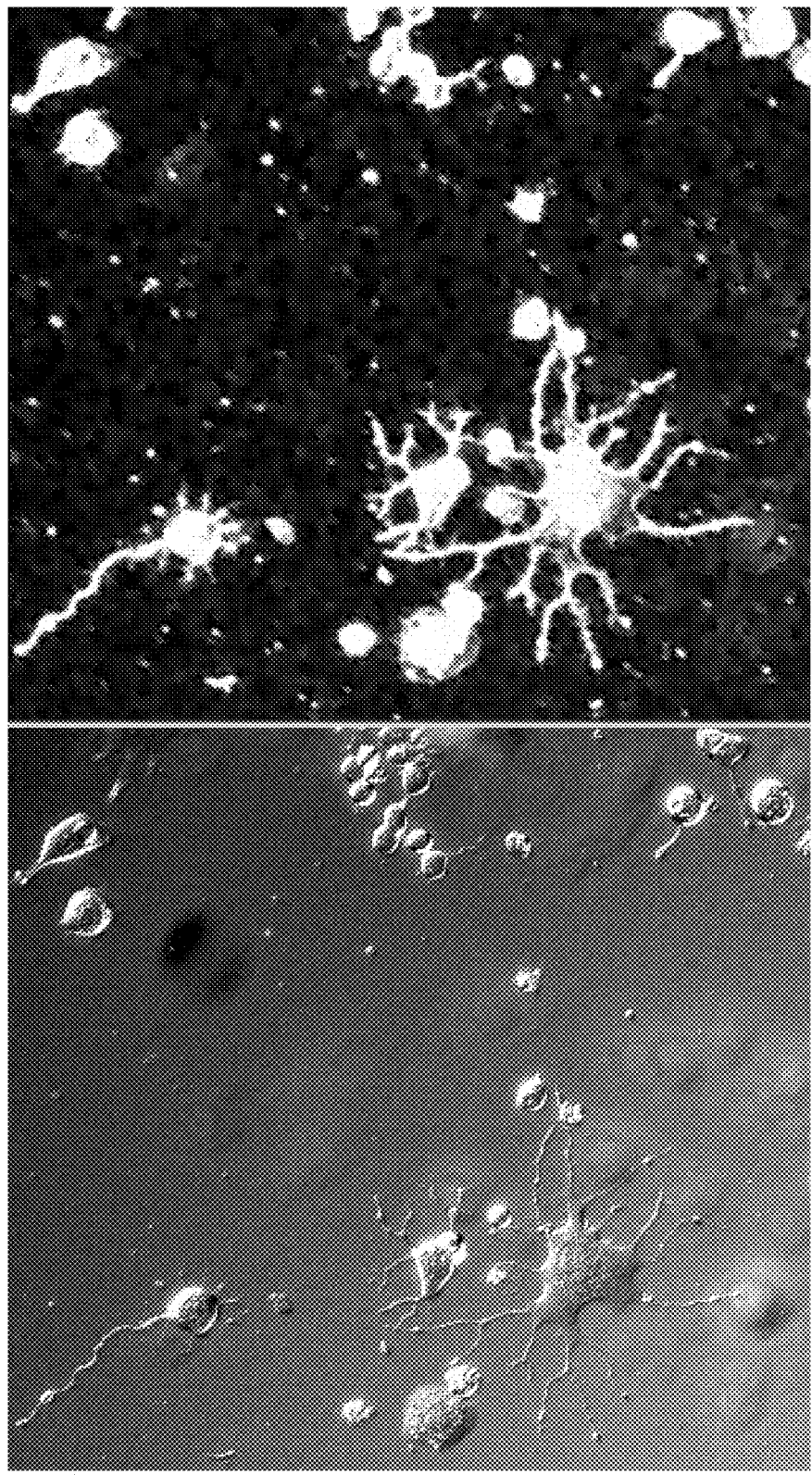
FIG. 5a shows an unstained cell image, as imaged using differential interference contrast microscopy, and an energy texture transform of the image preprocessing procedures yields the image in FIG. 5b, in which neurites are enhanced and more easily detected by an automated system.

FIG. 4 is a flow chart showing the image preprocessing procedures used within the method for automated neurite analysis. Original image 110' is sent to decision point 111. If image 110' is fluorescently labeled it proceeds directly to nonlinear suppression 114 (Process 1—this process and all other numbered processes are described below in further details). If original image 110' is unlabeled, it is subjected to texture transform 112 (Process 6) to create image 113, which is then subjected to nonlinear suppression 114 (Process 1). Image 115 is output from suppression 114.

Image 115 is subjected to adaptive noise smoothing 116 (Process 2) and output as preprocessed neurite image 117.

FIG. 5a shows an unstained cell image, as imaged using differential interference contrast microscopy, and an energy texture transform yields the image in FIG. 5b, in which neurites are enhanced relative to other image components. It is the object of this figure to show that the energy texture transform of the present method yields an image in which neurites are more easily segmented by automated procedures.

Figure 6:
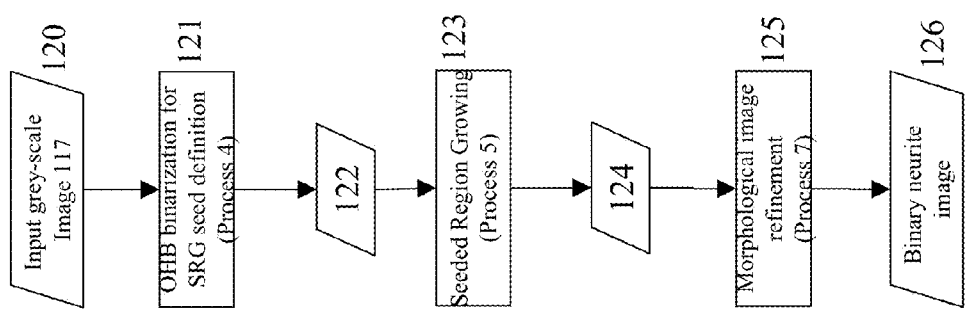
FIG. 6 is a flow chart illustrating the binarization procedure of the neurite analysis method.
Figure 7:
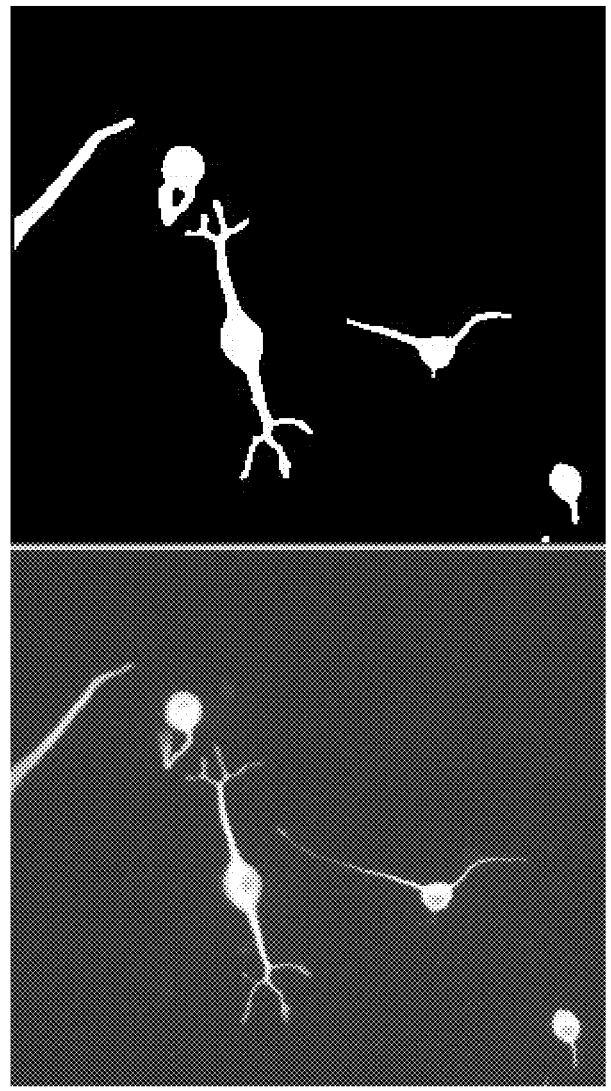
FIG. 7a shows an original image (acquired using fluorescence microscopy)
FIG. 7b shows a binary neurite image in which both neurites and cell bodies have been binarized accurately and automatically by the binarization procedures of the present method.

FIG. 6 is a flow chart illustrating the binarization procedure of the neurite analysis method. At 120, image 117 is input. At 121, preprocessed neurite image 117 is binarized by histogram bipartition (Process 4). Binary image 122 is output. At 123, image 122 serves as a seed for a SRG procedure (Process 5). Region image 124 is output. At 125, region image 124 is subjected to morphological image refinement (Process 7) to remove small holes and smooth boundaries. Binary neurite image 126 is output, as shown in FIG. 7.

FIG. 7a shows an original image (acquired using fluorescence microscopy), and FIG. 7b shows a binary neurite image 126 in which both neurites and cell bodies have been binarized accurately by the present method. It is the object of this figure to show that the binarization process of the present method leads to accurate segmentation of neurites and cell bodies.

Figure 8:
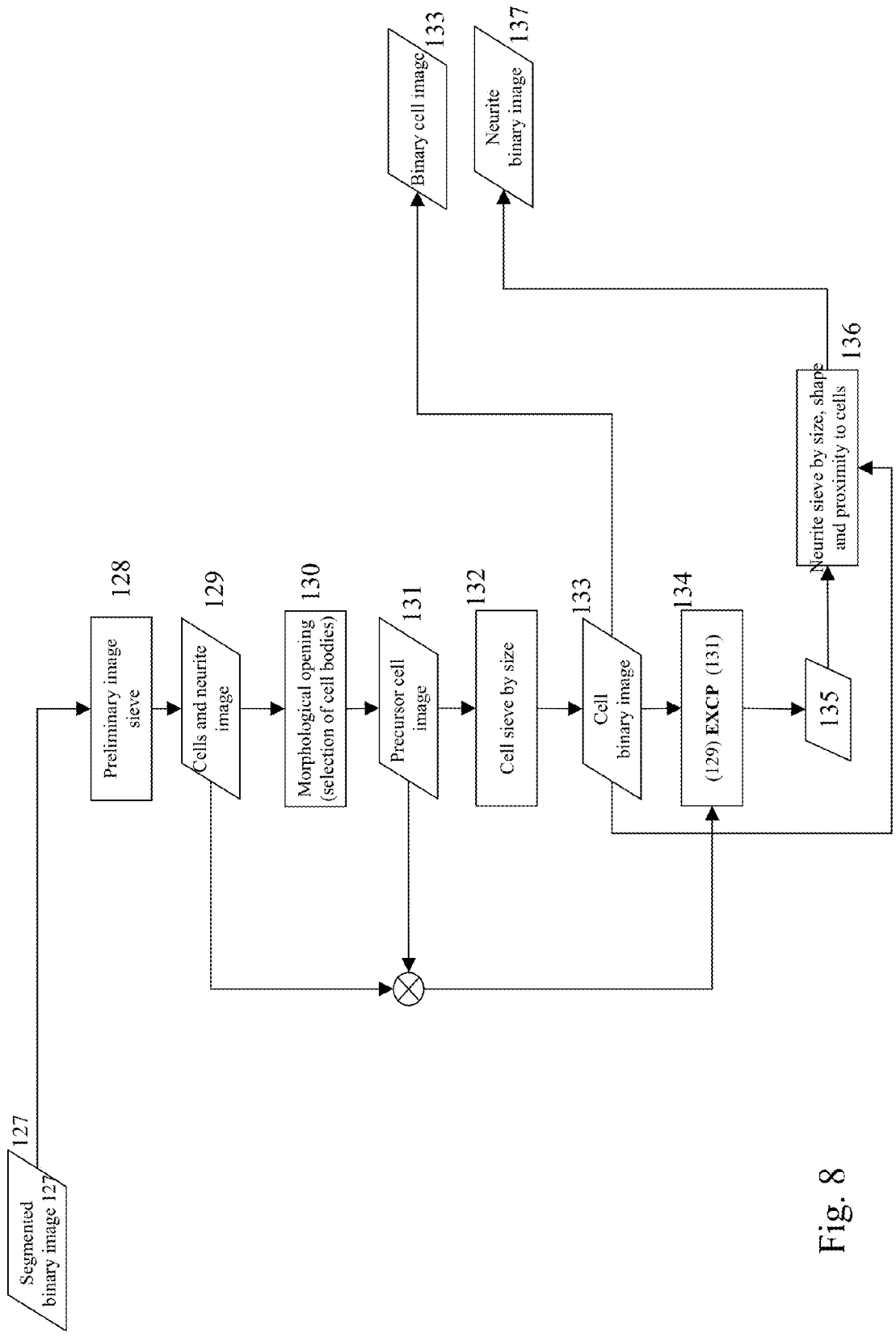
FIG. 8 is a flow chart illustrating the cell and neurite classification procedure of the present method.

FIG. 8 is a flow chart illustrating the cell and neurite classification procedure of the present method. At 127, image 126 is input. At 128, image 126 is sieved by a multicriterion process (Process 13). Sieve 128 removes objects with shape and area which are not characteristic of neurites or cells. Sieve 128 outputs image 129 containing both cells and neurites. At 130, image 129 is subjected to a morphological opening process. Precursor image 131 is output.

At 132, a sieve by size (Process 13) is applied to image 131. The output of sieve 132 is binary cell image 133, which contains only objects which are larger than a minimal cell size.

At 134, precursor image 131 is logically excluded from cell and neurite image 129. This results in image 135 containing only neurites. At 136, image 135 is sieved by a multicriterion process including size, shape and proximity (Process 13), to create binary neurite image 137. In image 137, only objects with neurite shape and size and which are proximal to cell bodies (as demonstrated in image 133) are present.

Figure 9:
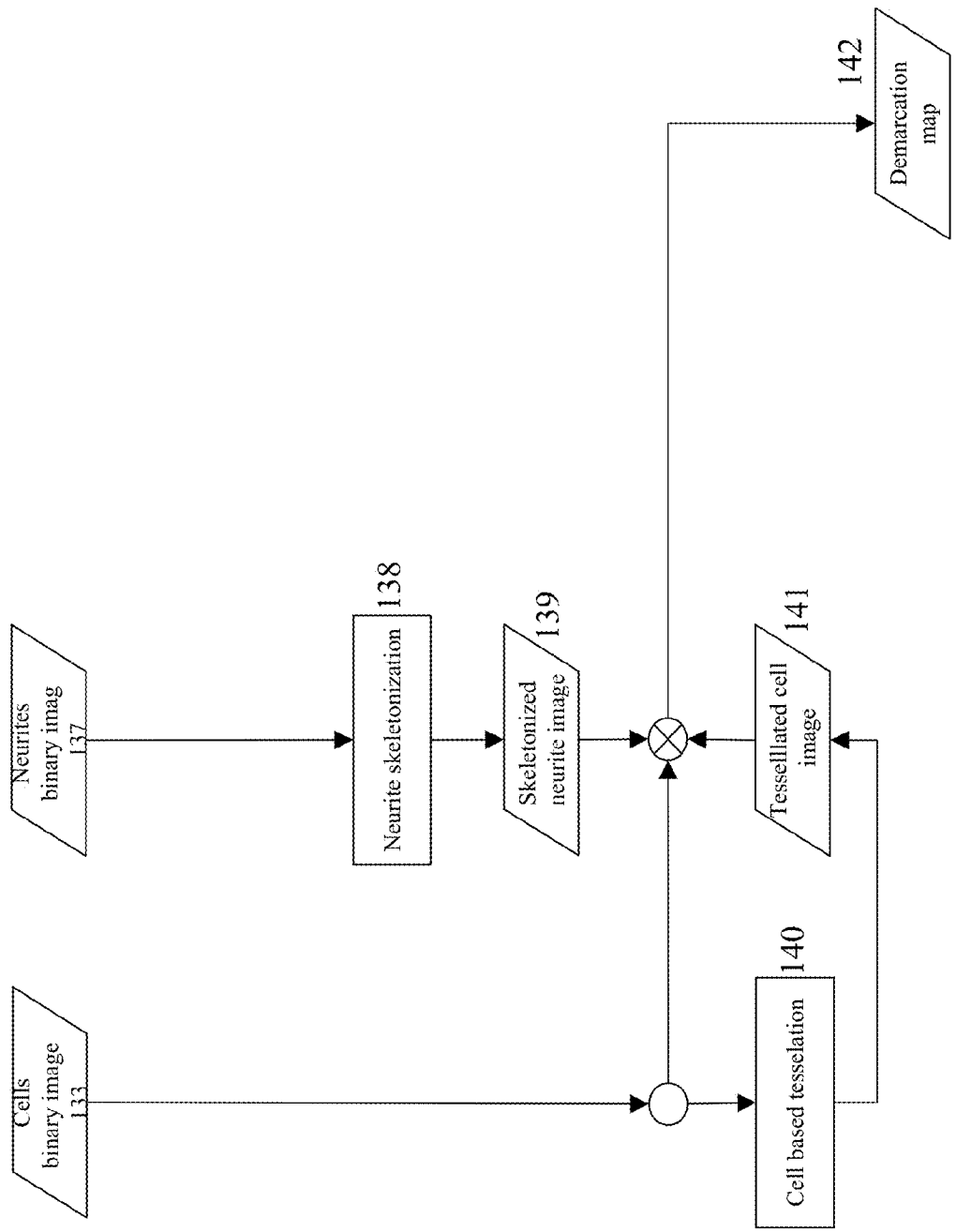
FIG. 9 is a flow chart illustrating the demarcation mapping procedure of the present method.

FIG. 9 is a flow chart illustrating the demarcation mapping procedure of the present method. At 138, binary neurite image 137 is skeletonized to create skeletonized neurite image 139.

Figure 10:
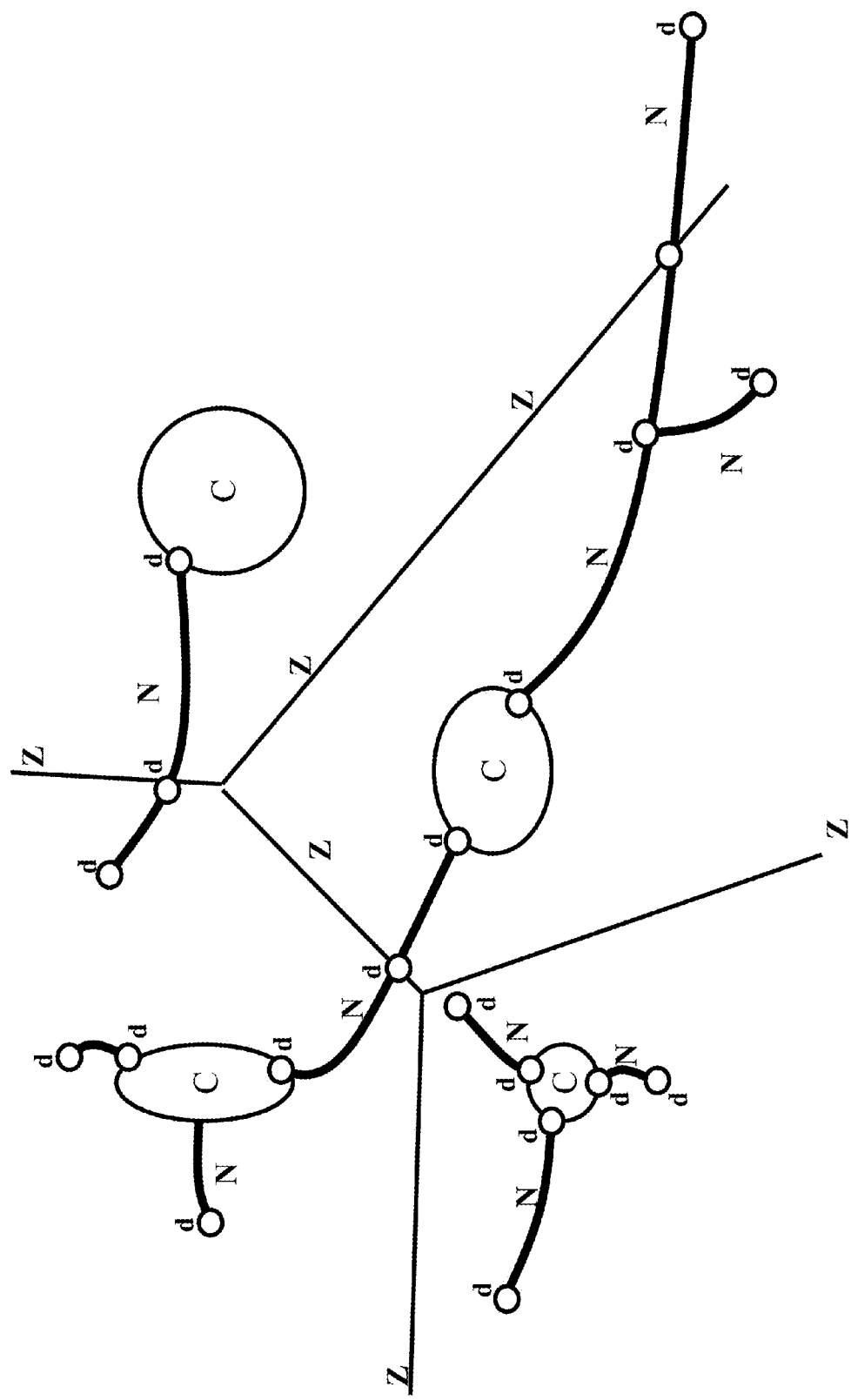
FIG. 10 illustrates zones of influence within which neurites and details of neurite geometry are assigned, during the automated demarcation mapping procedure for localizing specific neurites and their geometrical properties to cells of origin.

At 140, a tessellation procedure is applied to binary cell image 133 to create tessellated cell image 141 consisting of zones of influence of cell bodies (see FIG. 10). These zones of influence are geometrically defined areas around each cell, within which neurites can be assigned to cells of origin.

At 142, neurites and details of neurite geometry (end points, branch points, attachment points and so forth) are determined in skeletonized neurite image 139. Using cell image 133 and tessellated image 141, neurites and details of neurites may be assigned to cells of origins.

FIG. 10 illustrates zones of influence within which neurites and details of neurite geometry are assigned. "C" labels denote cell bodies. "N" labels define neurite skeletons. "Z" labels denote boundaries of influence zones. "d" labels denote details of neurite geometry. It is the object of this figure to show that the demarcation mapping of the present method is effective in both creating zones around each cell, and in localizing the origins of neurites and their geometric features. Within the zone of each cell, the neurites and their features that are shown may be related to the cell of origin for that zone.

FIG. 11, on the left, shows a flow chart for the granule segmentation of the analysis of granular translocation assays. Original image 210 is subjected to a set of procedures which include image preprocessing, binarization, and quantification.

FIG. 11, on the right, shows a flow chart for the cytoplasm segmentation of the analysis of granular translocation assays. Original image 200 is subjected to a set of procedures which include image preprocessing, binarization, seeded region growing, morphological refinement, sieving and quantification.

Figure 12:
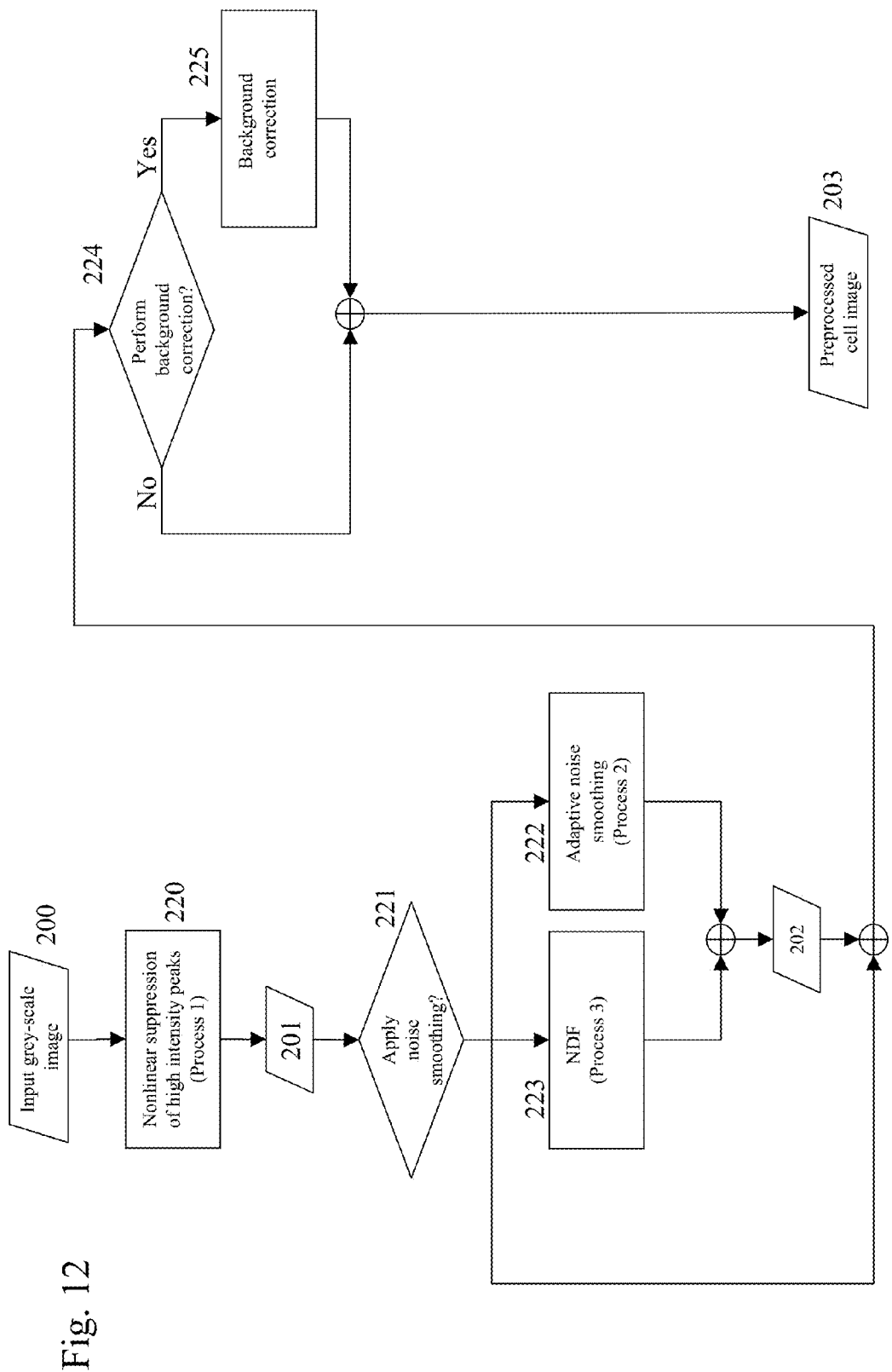
FIG. 12 is a flow chart illustrating the image preprocessing of cell body segmentation of the method for analysis of granular translocation assays.

FIG. 12 is a flow chart illustrating the image preprocessing of cell body segmentation of the method for analysis of granular translocation assays. Original image 200 is subjected to nonlinear suppression 220 (Process 1). Output image 201 is then sent to decision point 221. If output image 201 is noisy, it is subjected to adaptive noise smoothing 222 (Process 2) or nonlinear diffusion filtering 223 (Process 3) to produce image 202. Preferably, filtering 223 is achieved by iterations of SGMD and AEED processing. If image 201 is not noisy, it proceeds directly to process 224. At 224, a decision is made whether image 201 or 202 should be subjected to background correction 225 (Process 12). Preprocessed cell image 203 is produced.

Figure 13:
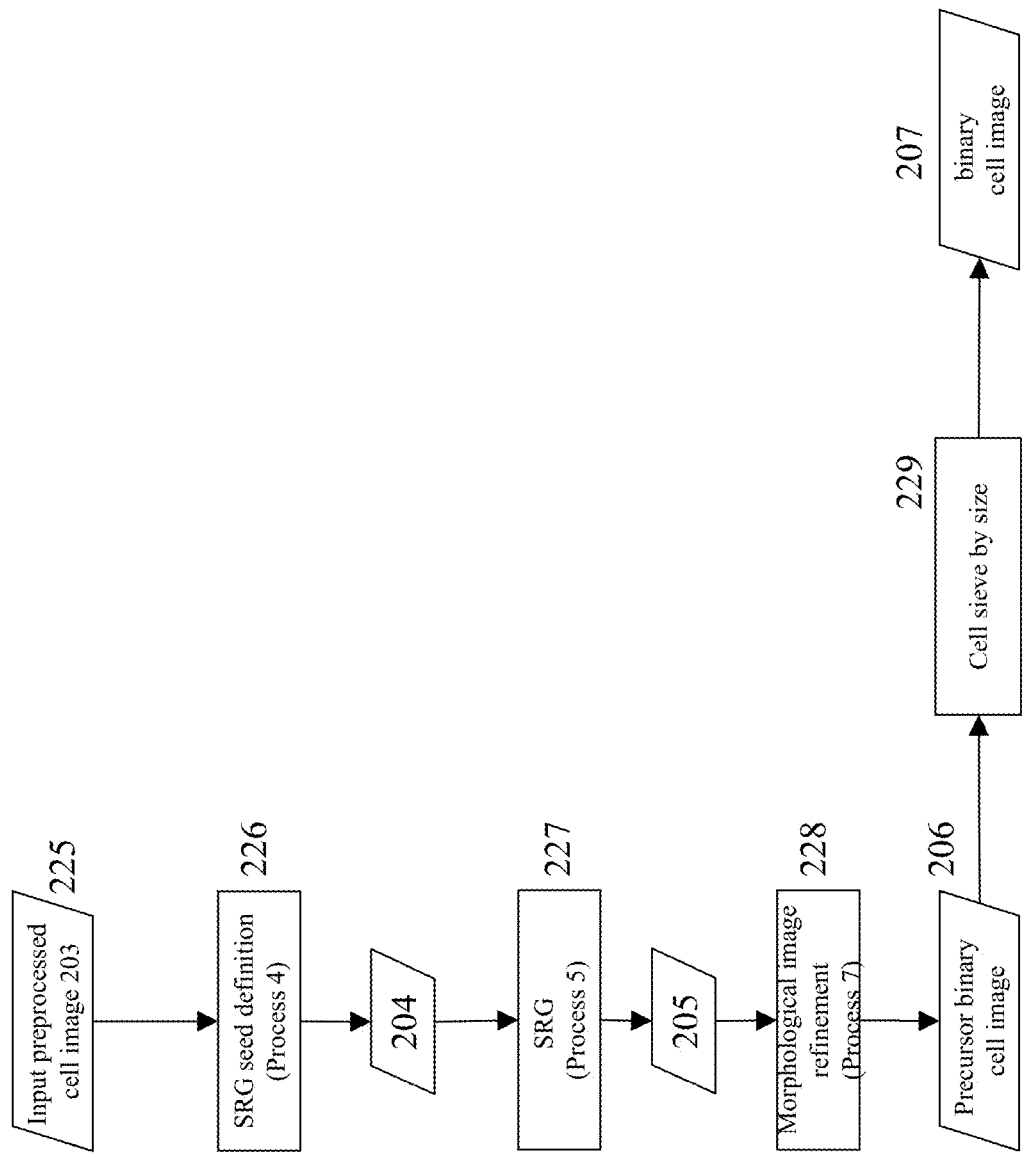
FIG. 13 is a flow chart illustrating the binarization, seeded region growing, morphological refinement and sieving procedures of the cell body segmentation of the method for analysis of granular translocation assays.

FIG. 13 is a flow chart illustrating the binarization, seeded region growing, morphological refinement and sieving procedures of the cell body segmentation of the method for analysis of granular translocation assays. At 225', preprocessed cell mage 203 is input. At 226, image 203 is binarized by OHB (Process 4) to yield binary seed image 204. At 227, image 204 is subjected to SRG (Process 5) to yield region image 205. At 228, region image 205 is subjected to morphological refinement (Process 7) and refined precursor cell image 206 is output. At 229, refined cell image 206 is subjected to a sieve by size (Process 13) which generates binary cell image 207. Cell image 207 does not contain objects smaller than the minimal cell size.

Figure 14:
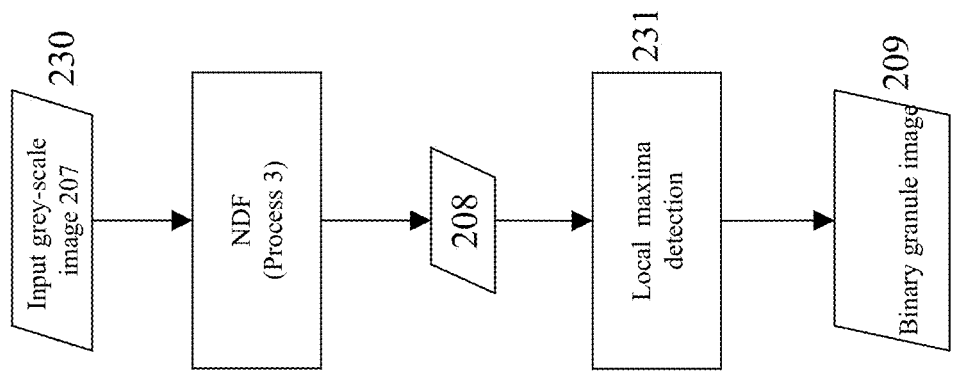
FIG. 14 is a flow chart illustrating the granular segmentation procedures of the method for analysis of granular translocation assays.

FIG. 14 is a flow chart illustrating the granular segmentation procedures of the method for analysis of granular translocation assays. Binary cell image 207 is subjected to nonlinear diffusion filtering 230 (Process 3) to generate output image 208. Preferably, diffusion filtering is by SPED processing. Enhanced intensity peaks in image 208 correspond to vesicles and are detected as local maxima at 231, to generate binary granule image 209.

Figure 15:
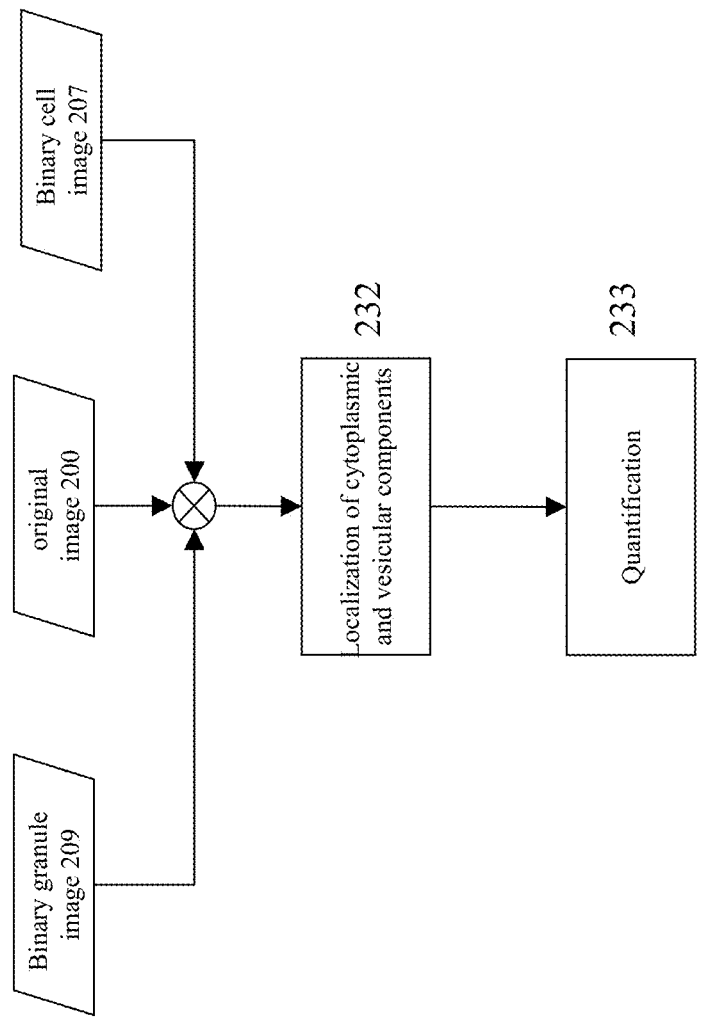
FIG. 15 is a flow chart illustrating the quantification procedures of the method for analysis of granular translocation assays.

FIG. 15 is a flow chart illustrating the quantification procedures of the method for analysis of granular translocation assays. At 232, binary granule image 209 and binary cell image 207 are used to locate cytoplasmic and vesicular (granules within cytoplasm) components in original image 200. From the located components of image 200, any form of intensity or spatially-based analysis may be conducted. Preferably, quantification by local contrast (Process 8) and/or distributional feature analysis (Process 9) and/or frequency domain analysis (Process 10, FIG. 16) is performed at quantification 233.

Figure 16:
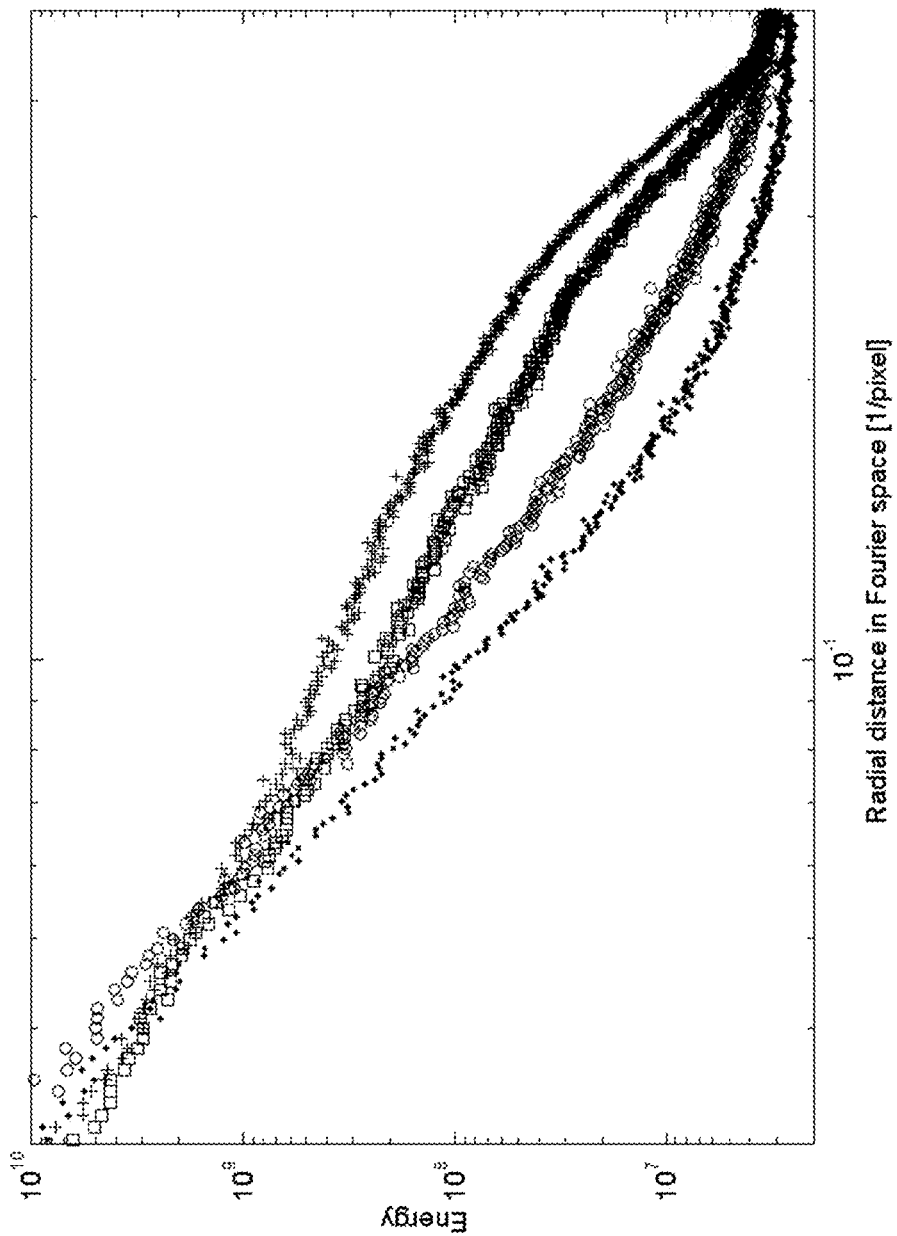
FIG. 16 illustrates data from the frequency domain analysis method of quantification, demonstrating that frequency domain discrimination of granular alterations in treated cells is a viable alternative to other methods such as measuring area of granular material.

FIG. 16 illustrates a frequency domain analysis (Process 10) of quantification 233, demonstrating discrimination of granular alterations in treated cells. Differences in intracellular granular material are detected from the Fourier spectra of cell images. The energy spectrum of control cells is depicted by dots (lower curve), while the spectra of cells treated with three doses of a drug and containing granules of increasing quantity and size are depicted by circles, squares and crosses, correspondingly. This figure shows that biologically relevant effects may be discriminated by the spatial domain analysis of the present method.

Figure 17:
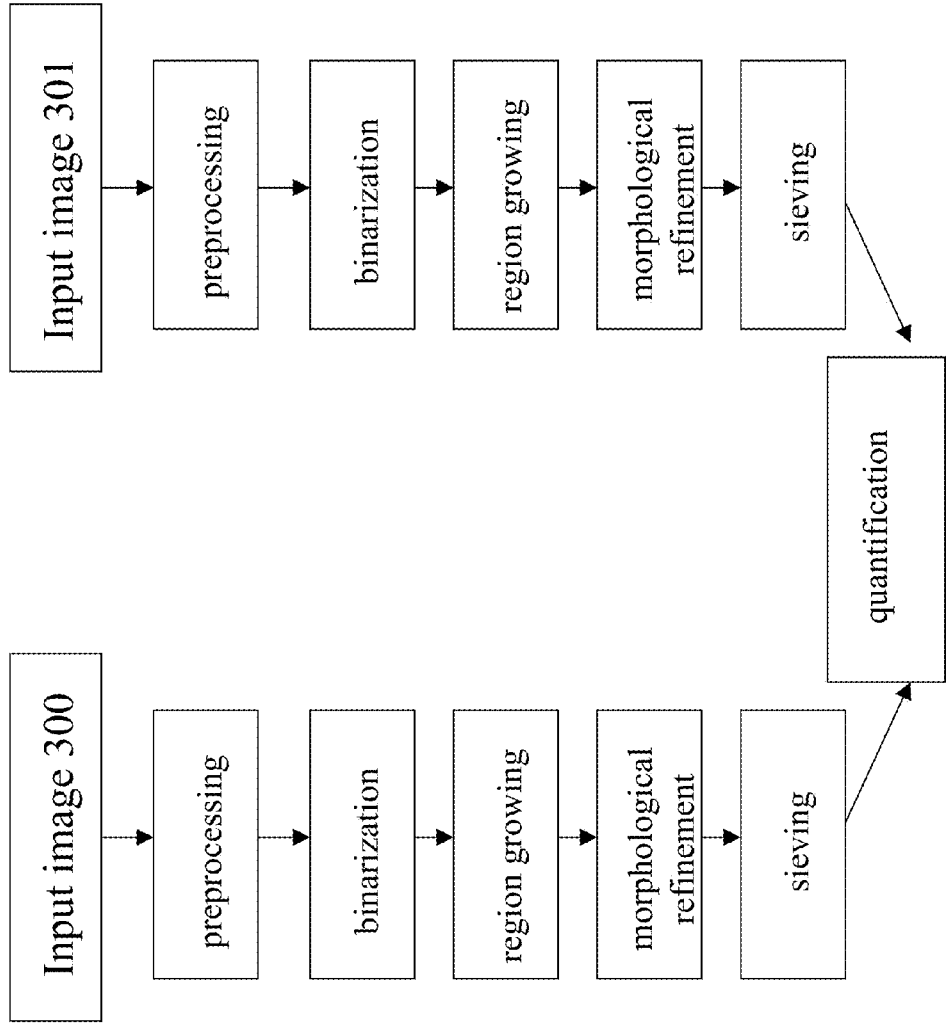
FIG. 17 is a flow chart illustrating the process for analysis of nuclear translocation.

FIG. 17 is a flow chart illustrating the process for analysis of nuclear translocation. Original image 300 is an image which best demonstrates the nuclei as a geometrical positioning aid. Original image 301 is an image which best shows the labeled molecule of interest, with fluorescence intensity corresponding to the local concentration of the labeled molecule. Preferably, differential visualization of nuclei and non-nuclear cell compartments in image 300 and image 301 is accomplished by different conditions of excitation and emission filtering on the microscope.

Image 300 (FIG. 17 left) is subjected to a set of procedures which segment nuclei. These procedures include image preprocessing, binarization, seeded region growing, morphological refinement, sieving and quantification.

Image 301 (FIG. 17 right) is subjected to a set of procedures which segment cytoplasm. These procedures include image preprocessing, binarization, seeded region growing, morphological refinement, sieving and quantification.

Figure 18:
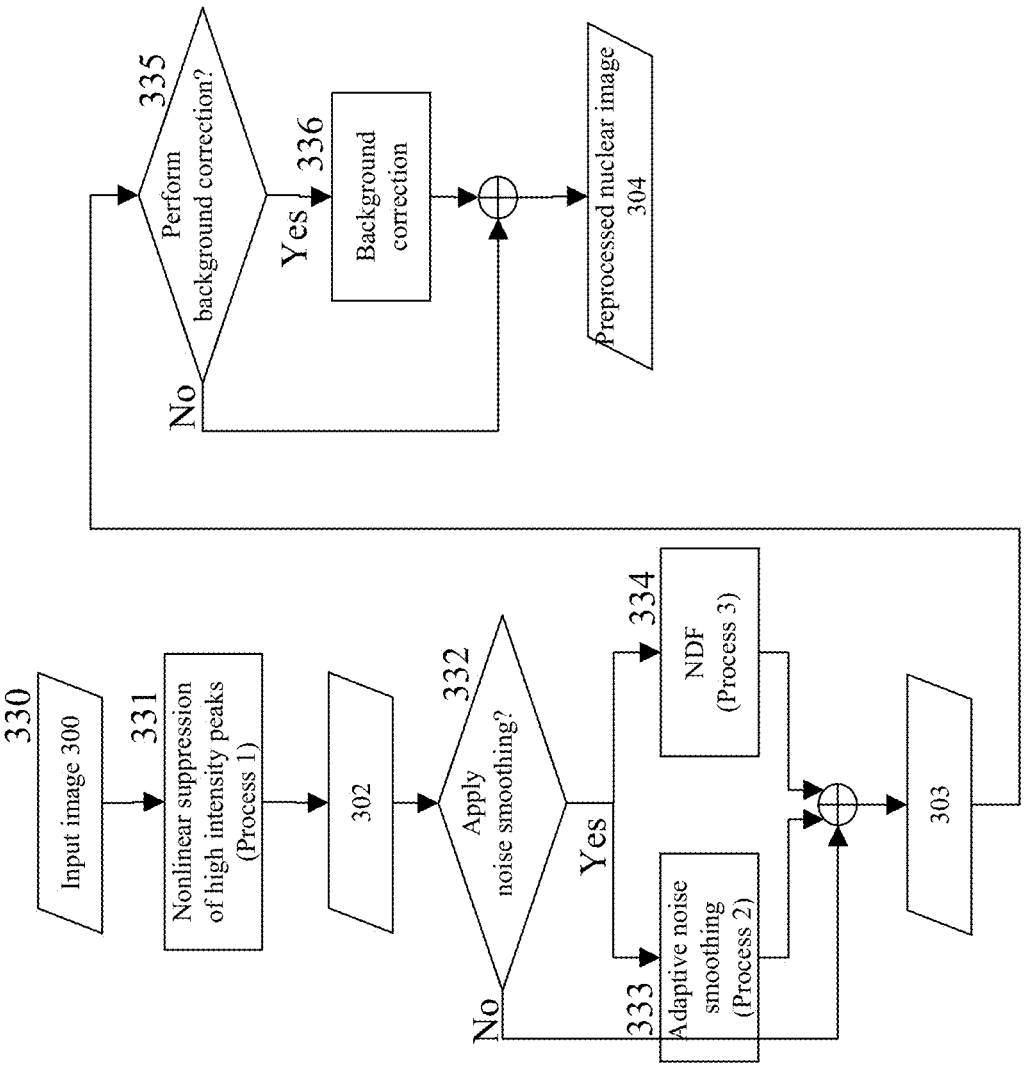
FIG. 18 is a flow chart illustrating the preprocessing stage of the nuclear segmentation used for analysis of nuclear translocation assays.

FIG. 18 is a flow chart illustrating the preprocessing stage of the nuclear segmentation used for analysis of nuclear translocation assays. Original image 300 is input at 330. At 331, image 300 is subjected to nonlinear suppression (Process 1) and image 302 is output. Image 302 is sent to decision point 332. If image 302 is noisy, it is subjected to adaptive noise smoothing 333 (Process 2) or nonlinear diffusion filtering 334 (Process 3). Preferably, filtering 334 is achieved by iterations of SGMD and AEED processing. Image 303 is output. Image 303 is sent to decision point 335. If background correction is desirable, image 303 is subjected to background correction 336 (Process 12). Preprocessed nuclear image 304 is produced.

Figure 19:
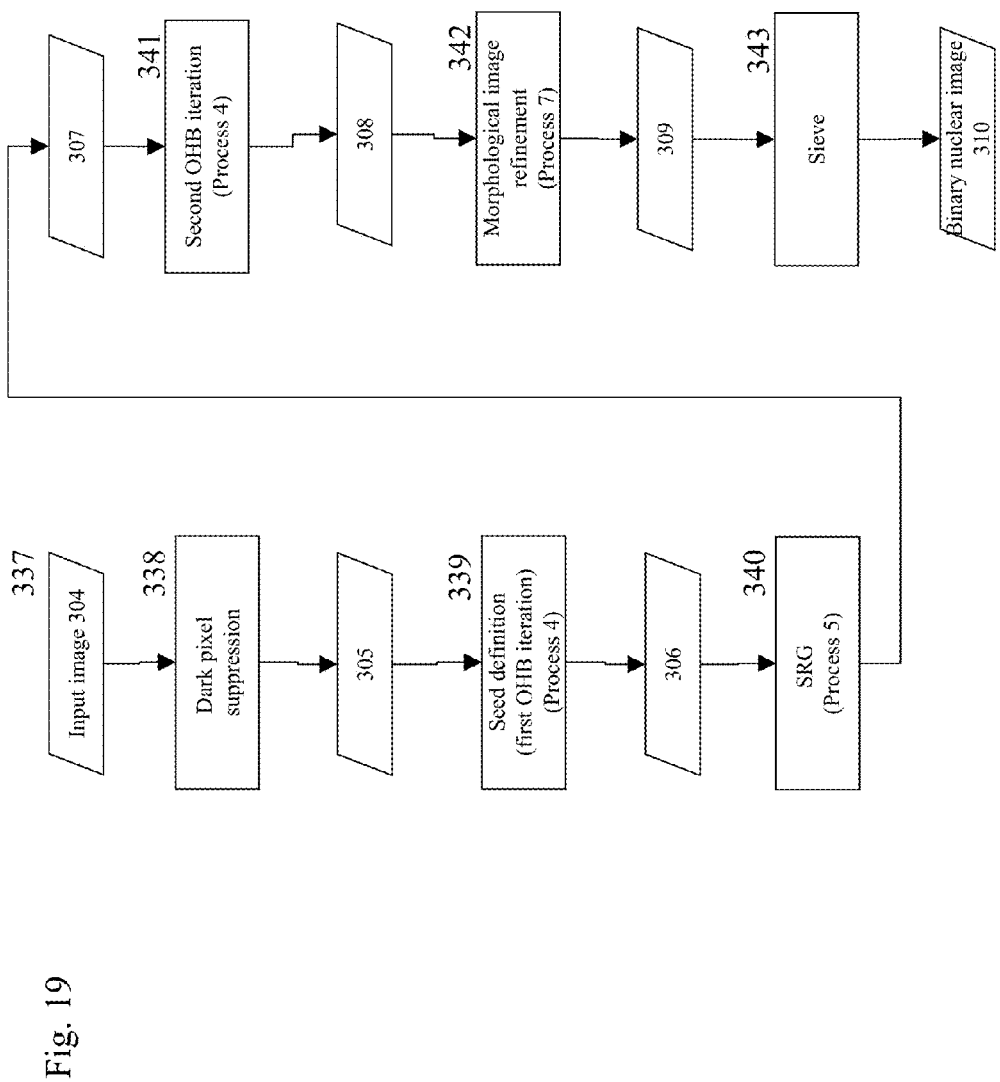
FIG. 19 is a flow chart illustrating the binarization, seeded region growing and morphological refinement processes of the nuclear segmentation of the method for analysis of nuclear translocation.

FIG. 19 shows the binarization, seeded region growing, morphological refinement and sieving processes of the nuclear segmentation used for analysis of nuclear translocation assays. At 337, image 304 is input. At 338, image 304 is subjected to a process in which nuclear image pixels darker than the most probable pixel value are set to the most probable pixel value. Image 305 is output. At 339, image 305 is binarized by OHB (Process 4) and image 306 is output. At 340, image 306 is subjected to SRG (Process 5) to yield region image 307. At 341, region image 307 is used as a mask to define pixels for a second iteration of OHB (Process 4) performed on image 305. Binary image 308 is output, and provides a more precise definition of nuclear boundaries than does region image 307. At 342 image 308 is subjected to morphological refinement (Process 7). Image 309 is output. At 343, image 309 is sieved (Process 13). Sieve 343 removes objects smaller than a minimum nuclear size, said objects being confusable with nuclei if not removed. Binary nuclear image 310 is output.

Figure 20:
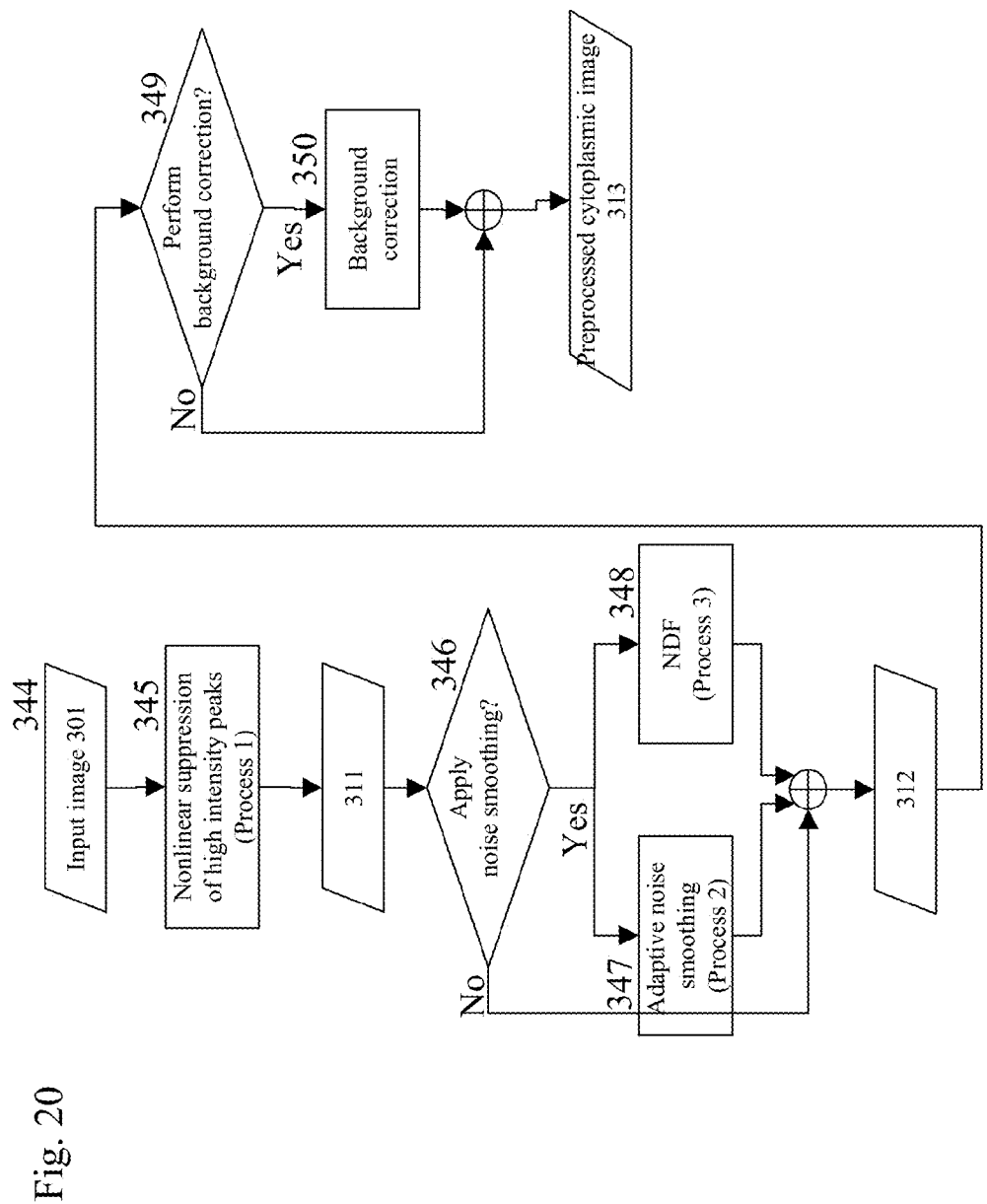
FIG. 20 is a flow chart illustrating the preprocessing of the cytoplasmic segmentation used for analysis of nuclear translocation assays.

FIG. 20 is a flow chart illustrating the preprocessing of the cytoplasmic segmentation used for analysis of nuclear translocation assays. At 344, cytoplasmic image 301 is input. Image 301 is subjected to nonlinear suppression at 345 (Process 1). Image 311 is output. Image 311 is sent to decision point 346. If image 311 is noisy, it is subjected to adaptive noise smoothing 347 (Process 2) or nonlinear diffusion filtering 348 (Process 3). Preferably, filtering 348 is achieved by iterations of SGMD and AEED processing. Image 312 is output. Image 312 is sent to decision point 349. If background correction is desirable, image 312 is subjected to background correction 350 (Process 12). Preprocessed cytoplasmic image 313 is produced.

Figure 21:
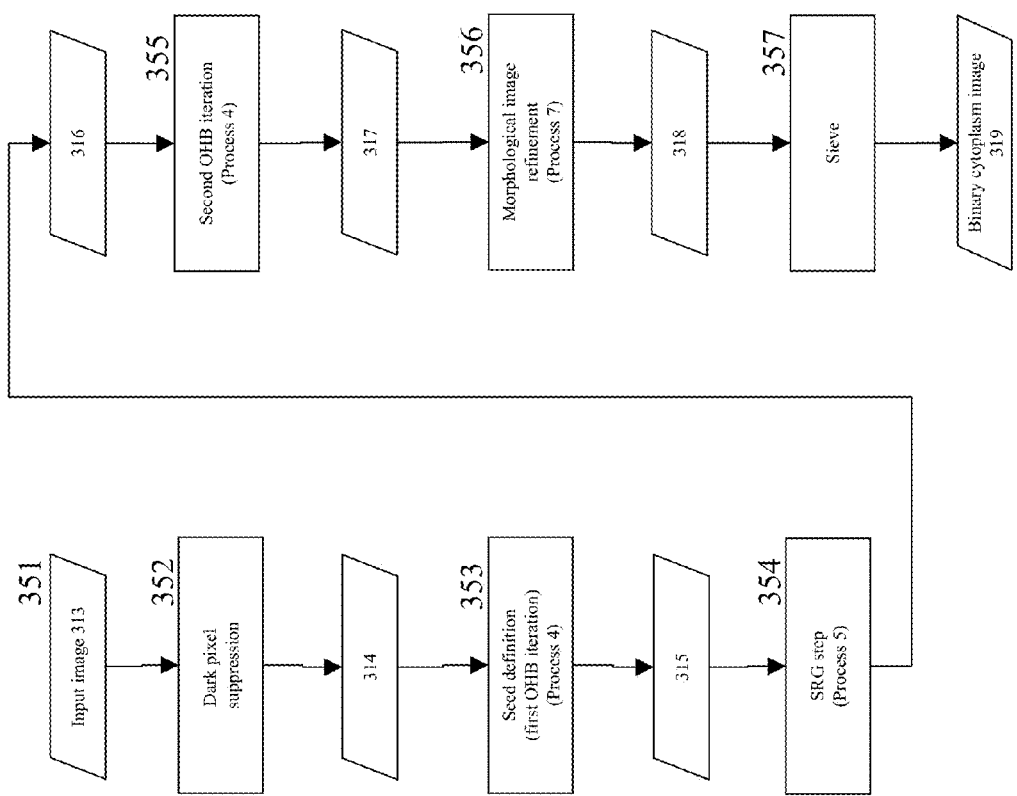
FIG. 21 is a flow chart illustrating the binarization, seeded region growing, morphological refinement and sieving processes of the cytoplasmic segmentation used in the method for analysis of nuclear translocation assays.

FIG. 21 is a flow chart illustrating the binarization, seeded region growing, morphological refinement and sieving processes of the cytoplasmic segmentation used in the method for analysis of nuclear translocation assays. At 351, image 313 is input. At 352, image 313 is subjected to a process in which nuclear image pixels darker than the most probable pixel value are set to the most probable pixel value. Image 314 is output. At 353, image 314 is binarized by OHB (Process 4) and seed image 315 is output. At 354, image 315 is subjected to SRG (Process 5) to yield region image 316. At 355, region image 316 is used as a mask to define pixels for a second iteration of OHB (Process 4) performed on image 314. Binary image 317 is output, and provides a more precise definition of nuclear boundaries (for nuclear exclusion) than does region image 316. At 356 image 317 is subjected to morphological refinement (Process 7). Image 318 is output. At 357, image 318 is sieved (Process 13). Sieve 357 removes objects smaller than a minimum cell size, said objects being confusable with cells if not removed. Binary cytoplasm image 319 is output.

Figure 22:
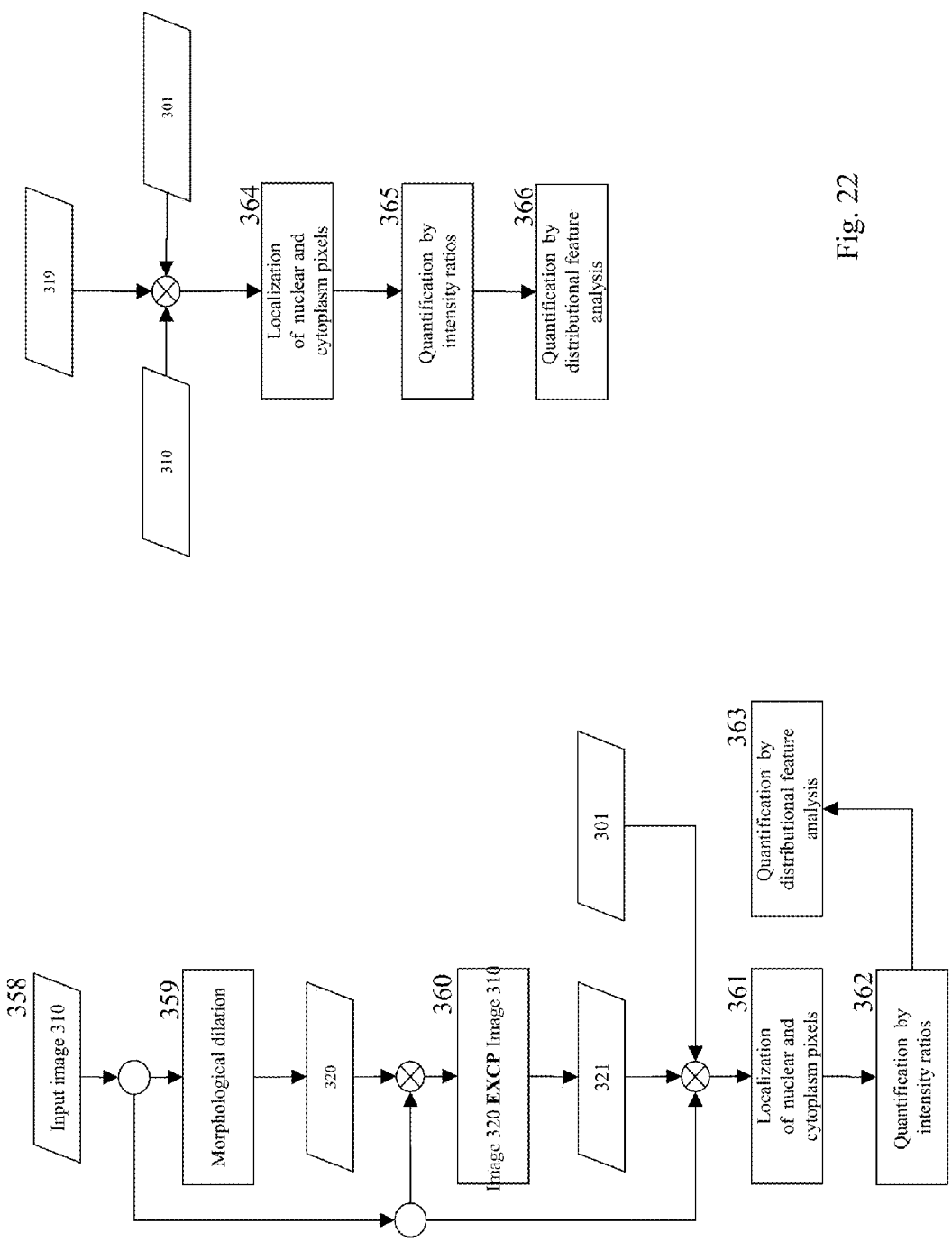
FIG. 22 is a flow chart illustrating the quantification procedure used in the method for analysis of nuclear translocation assays.

FIG. 22 is a flow chart illustrating the quantification procedure used in the method for analysis of nuclear translocation assays. In one aspect, quantification uses segmented nuclei as an origin. Intensity data are then read from original cytoplasm image 301, at fixed locations defined by proximity to nuclei (e.g. a collar starting at 2 pixels from the nucleus and extending to 6 pixels from the nucleus).

At 358 binary nuclear image 310 is input. Preferably, at 359, image 310 is subjected to a morphological dilation operation (as disclosed in Russ 1999, p. 460 and Parker 1997, p. 68) to generate dilated binary nuclear image 320. Preferably, the dilation is performed with a circular structural element (as disclosed in Parker 1997, p. 73). Image 320 is composed of both the nuclear component of binary nuclear image 310, and a peri-nuclear component created by the dilation process.

At 360, image 310 is excluded from image 320 to leave image 321, containing just the peri-nuclear component.

At 361, image 310 serves as a mask for identifying nuclear pixels in cytoplasm image 301, and image 321 serves as a mask for identifying peri-nuclear pixels in cytoplasm image 301.

Preferably, at 362, translocation is quantified from a ratio of peri-nuclear label intensity and nuclear label intensity (Process 8). In another preferable aspect, at 363, quantification includes distributional feature analysis (Process 9) of ratios 362.

In another aspect, at 364, binary cytoplasm image 319 is used to identify cytoplasmic pixels in cytoplasm image 301, and cytoplasmic pixel intensities are calculated from these identified pixels. At 364, binary nuclear image 310 serves as a mask for identifying nuclear regions within cytoplasmic image 301, and nuclear pixel intensities are calculated from these identified pixels. Preferably, at 365, translocation is quantified from a ratio of cytoplasmic label intensity inside the nucleus and in an area that includes as much as possible of the cytoplasm of that cell (Process 8). In another aspect, quantification can include distributional feature analysis 366 (Process 9) of ratios 365.

FIG. 23 is a flow chart illustrating the analysis of ruffle translocation. Original image 400 is an image which best demonstrates nuclei as a geometrical positioning aid. Original image 401 is an image which best shows the labeled molecule of interest, with fluorescence intensity corresponding to the local concentration of the labeled molecule. Preferably, differential visualization of nuclei and non-nuclear cell compartments in image 400 and image 401 is accomplished by different conditions of excitation and emission filtering on the microscope.

Image 400 (FIG. 23 left) is subjected to a set of procedures which segment nuclei. These procedures include image preprocessing, binarization, seeded region growing, morphological refinement and sieving.

Image 401 (FIG. 23 right) is subjected to a set of procedures which segment cytoplasm including ruffles. These procedures include image preprocessing, binarization, seeded region growing, morphological refinement and sieving.

Figure 24:
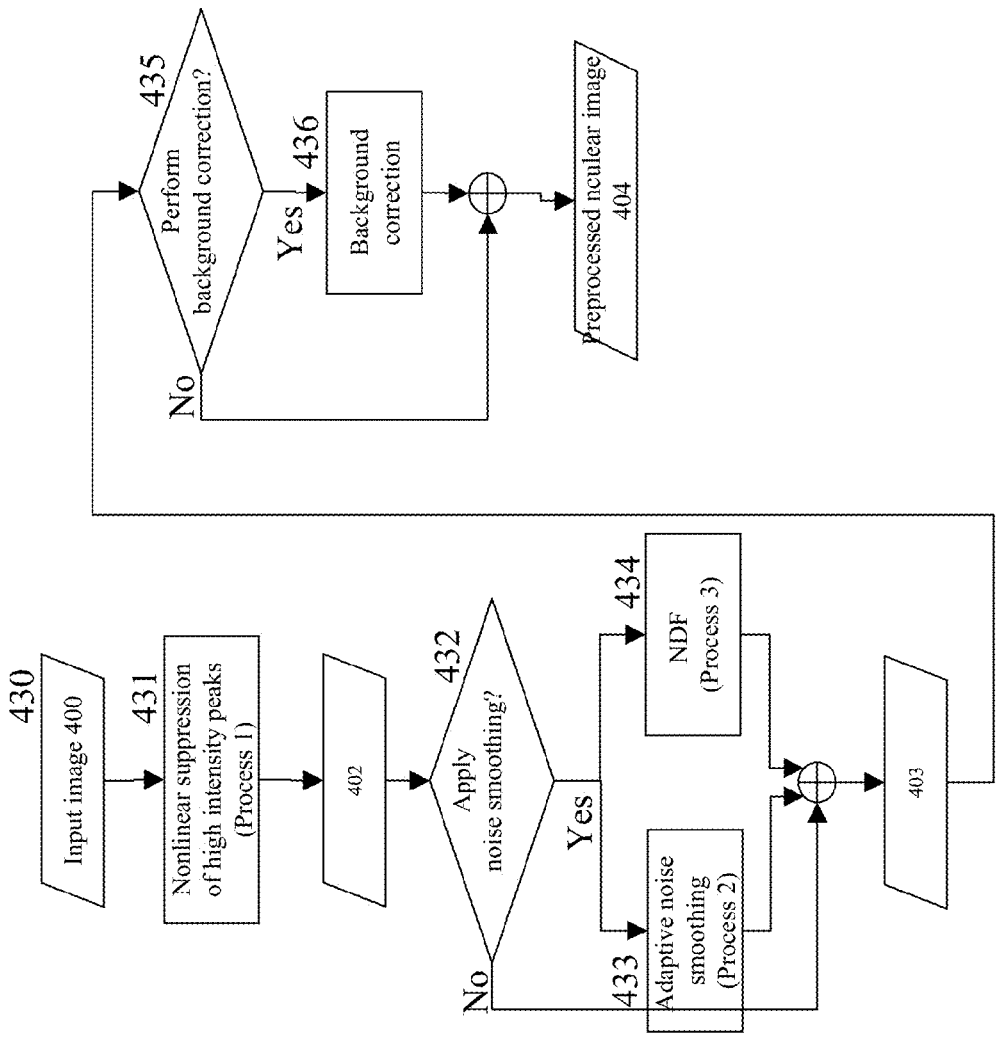
FIG. 24 is a flow chart illustrating the preprocessing stage of the nuclear segmentation used in the method for analysis of ruffle translocation assays.

FIG. 24 is a flow chart illustrating the preprocessing stage of the nuclear segmentation used in the method for analysis of ruffle translocation assays. Original image 400 is input at 430. At 431, image 400 is subjected to nonlinear suppression (Process 1) and image 402 is output. Image 402 is sent to decision point 432. If image 402 is noisy, it is subjected to adaptive noise smoothing 433 (Process 2) or nonlinear diffusion filtering 434 (Process 3). Preferably, filtering 434 is achieved by iterations of SGMD and AEED processing. Image 403 is output. Image 403 is sent to decision point 435. If background correction is desirable, image 403 is subjected to background correction 436 (Process 12). Preprocessed nuclear image 404 is produced.

Figure 25:
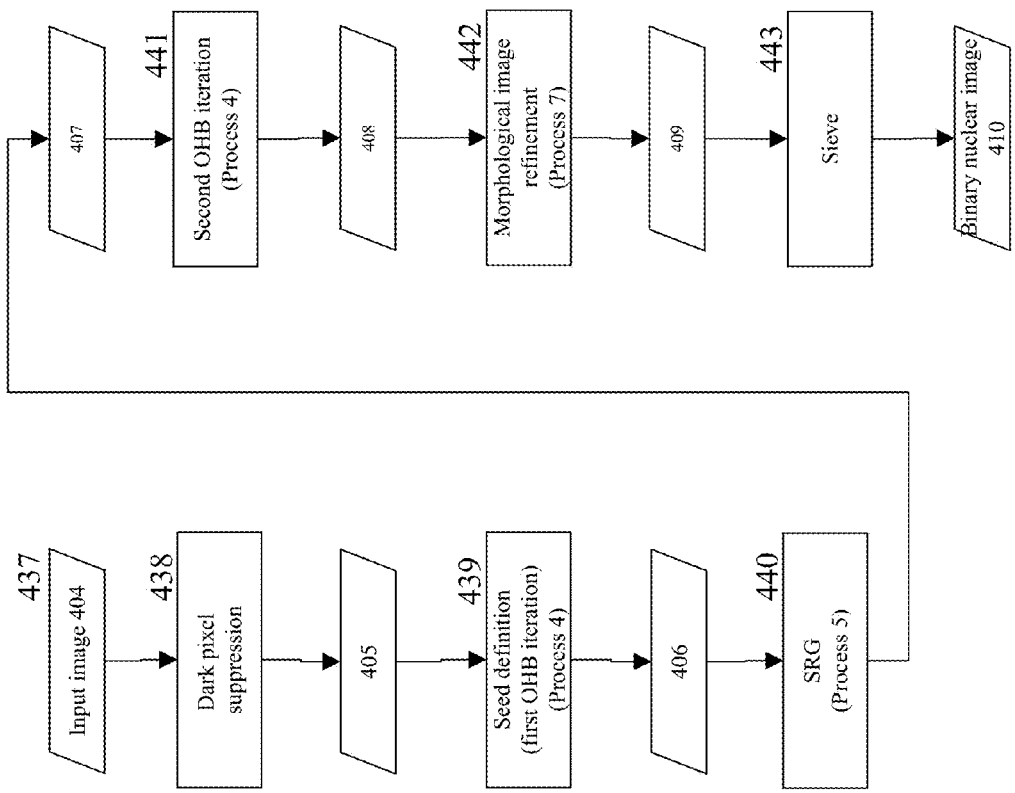
FIG. 25 is a flow chart illustrating the binarization, seeded region growing, morphological refinement and sieving processes of the nuclear segmentation used in the method for analysis of ruffle translocation.

FIG. 25 is a flow chart illustrating the binarization, seeded region growing, morphological refinement and sieving processes of the nuclear segmentation used in the method for analysis of ruffle translocation. At 437, image 404 is input. At 438, image 404 is subjected to a process in which nuclear image pixels darker than the most probable pixel value are set to the most probable pixel value. Image 405 is output. At 439, image 405 is binarized by OHB (Process 4) and image 406 is output. At 440, image 406 is subjected to SRG (Process 5) to yield region image 407. At 441, region image 407 is used as a mask to define pixels for a second iteration of OHB (Process 4) performed on image 405. Binary image 408 is output, and provides a more precise definition of nuclear boundaries than does region image 407. At 442 image 408 is subjected to morphological refinement (Process 7). Image 409 is output. At 443, image 409 is sieved (Process 13). Sieve 443 removes objects smaller than a minimum nuclear size, said objects being confusable with nuclei if not removed. Binary nuclear image 410 is output.

Figure 26:
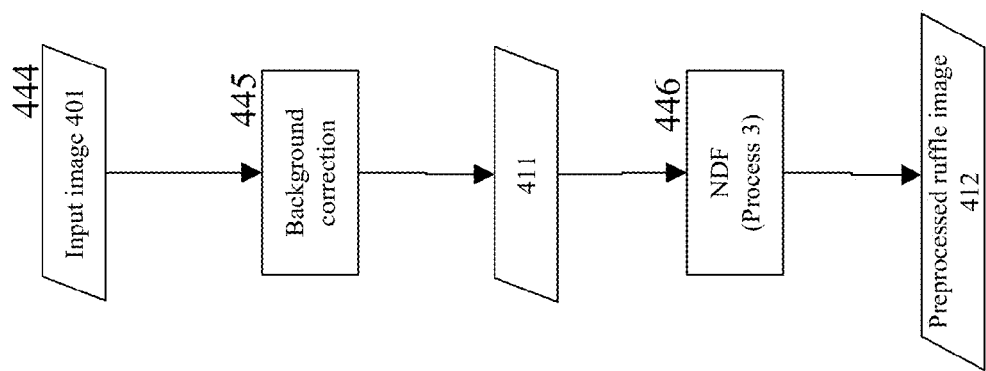
FIG. 26 is a flow chart illustrating the preprocessing stage of the cytoplasmic segmentation used for analysis of ruffle translocation assays.

FIG. 26 is a flow chart illustrating the preprocessing stage of the cytoplasmic segmentation used for analysis of ruffle translocation assays. At 444, cytoplasmic image 401 is input. At 445, image 401 is subjected to background correction (Process 12) which has the additional advantageous property that it emphasizes details of a size characteristic of ruffles. Image 411 is output. Image 411 is subjected to nonlinear diffusion filtering at 446 (Process 3). Preferably, filtering 446 is achieved by iterations of SGMD and AEED processing. Preprocessed ruffle image 412 is produced.

Figure 27:
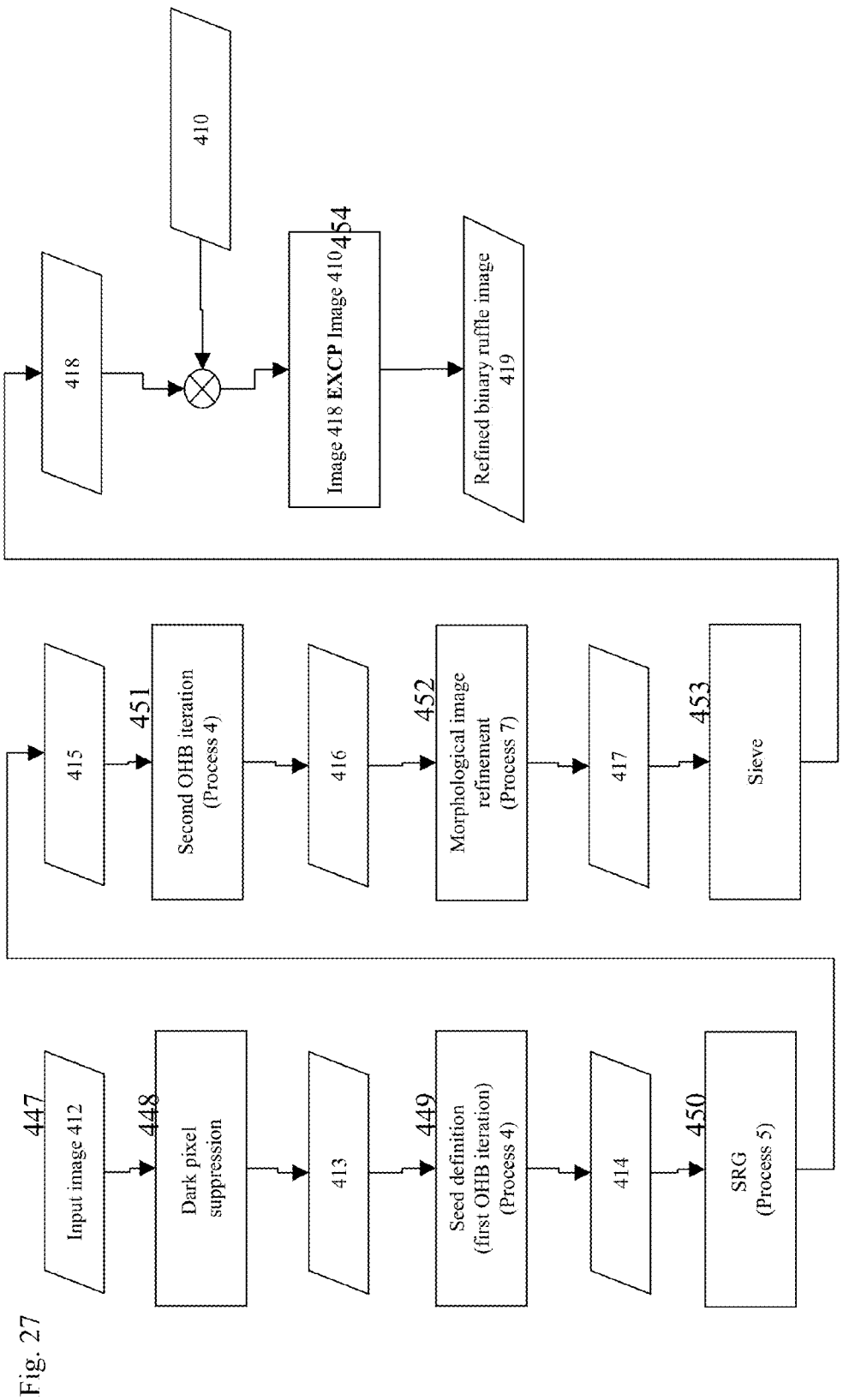
FIG. 27 is a flow chart illustrating the binarization, seeded region growing, morphological refinement and sieving processes of the ruffle segmentation used in the method for analysis of ruffle translocation assays.

FIG. 27 is a flow chart illustrating the binarization, seeded region growing, morphological refinement and sieving processes of the ruffle segmentation used in the method for analysis of ruffle translocation assays. At 447, preprocessed ruffle image 412 is input. At 448, image 412 is subjected to a process in which ruffle pixels darker than the most probable pixel value are set to the most probable pixel value. Image 413 is output. At 449, image 413 is binarized by OHB (Process 4) and image 414 is output. At 450, image 414 is subjected to SRG (Process 5) to yield region image 415. At 451, region image 415 is used as a mask to define pixels for a second iteration of OHB (Process 4) performed on image 413. Binary image 416 is output, and provides a more precise definition of ruffles than does region image 415. At 452 image 416 is subjected to morphological refinement (Process 7). Image 417 is output. At 453, image 417 is sieved (Process 13) by size to remove objects confusable with ruffles. Binary ruffle image 418 is output.

Preferably, at 454 binary nuclear image 410 is logically excluded from binary ruffle image 418 to create refined binary ruffle image 419 in which ruffles cannot be localized over nuclei.

Figure 28:
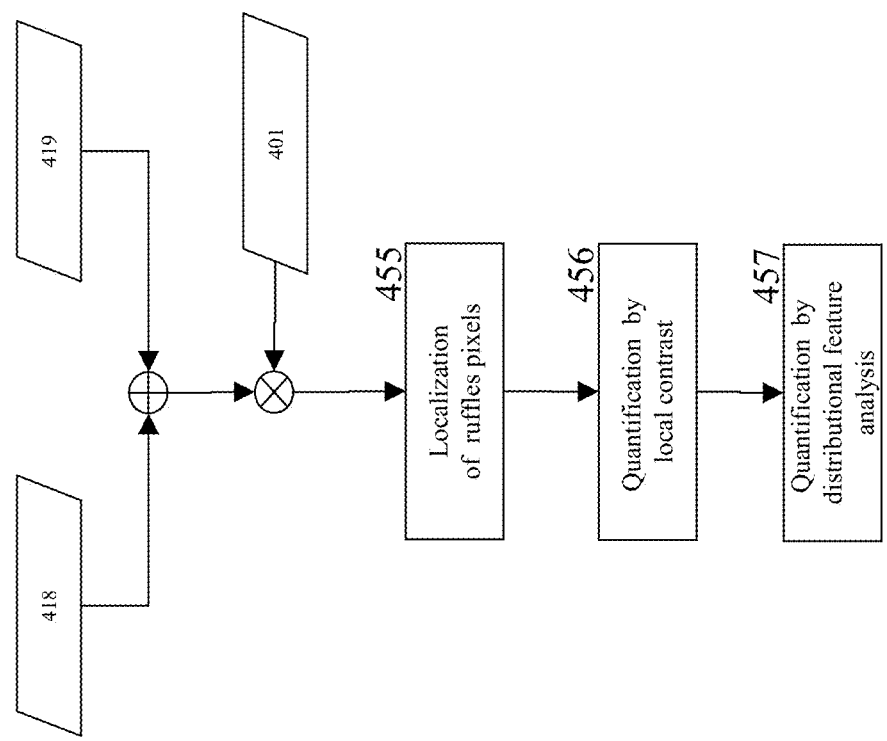
FIG. 28 is a flow chart illustrating the quantification procedure used for analysis of ruffle translocation assays.

FIG. 28 is a flow chart illustrating the quantification procedure used for analysis of ruffle translocation assays. At 455, binary ruffle image 418 or refined binary ruffle image 419 serves as a mask for calculation of ruffle intensity from cytoplasmic image 401. Preferably, at 456, quantification is achieved by local contrast (Process 8). In another aspect, quantification can include distributional feature analysis 457 (Process 9) based upon ruffle size and proximity.

Functions Used in the Methods of the Present Invention

The algorithmic steps of the methods are so devised as to best suit the characteristics of commonly used cell assays. The methods are constructed for each specific assay by integrating functions from the library described, below. While the general nature of the functions used in the methods of the present invention are given below, it is to be understood that any of these functions may be parameterized to optimally enhance, select, or otherwise affect features in images.

Process 1) Nonlinear Suppression of High Intensity Peaks

Artifacts arising from high intensity peaks can introduce undesirable variability of feature gray level statistics, and perturb adaptive threshold and region growing procedures. The peak suppression method is a variant of the known technique of histogram correction. As implemented in the present invention, the process takes the gray level reference image as input, and applies nonlinear suppression to the pixels with highest gray level values and an identity transform to the pixels within the rest of dynamic range. The output image exhibits a reduction in intensity variation over brighter objects, but not over less bright objects. This has the advantage that it improves the performance of subsequent image processing as described below.

Process 2) Adaptive Noise Smoothing

An adaptive noise smoothing procedure can be beneficial in improving feature detectability (and obvious to one skilled, e.g. as disclosed in Morrison et al., 1995). In a preferred aspect of the invention, a procedure is used which increases the image signal-to-noise ratio without compromising fine feature details. Original and Gaussian-smoothed images (U and $U\sigma$, respectively) are combined as shown in expression 2.1:

$$R = W \cdot U + (1-W) \cdot U\sigma, \quad (2.1)$$

where (R) is the result image and $W=W(|\nabla\sigma U|)$ is a weight function dependant upon the modulus of the Gaussian gradient $|\nabla\sigma U|$ of the original image, and $\sigma$ is the standard deviation of the Gaussian function used for smoothing.

Use of weight function W has the advantage that the pixels in result image R display values close to those of original image U in areas of high gradient magnitudes and to those of smoothed image $U_\sigma$ in areas with low gradient magnitudes. The areas of low gradient magnitude tend to contain a greater proportion of the image noise which is thereby reduced in relative amplitude.

Adaptive noise smoothing has the additional desirable property that noise in the output image has the same amplitude from image to image across a set of discretely acquired images. The advantage is that said amplitude uniformity of noise makes subsequent segmentation procedures operate more consistently.

Process 3) Adaptive Noise Smoothing And Feature Enhancement By Nonlinear Diffusion Filtering Nonlinear diffusion filtering (NDF) methods are members of the family of scale space techniques for image filtering. NDF methods (e.g. as disclosed in Weickert 1997) are useful where it is desirable to remove noise (defined as spatial modulations of high frequency) and preserve features with lower spatial frequency.

The present invention applies NDF methods to remove image noise, while relevant image features are enhanced in a fashion dependent upon their shape and size. An image is processed by iterative application of a nonlinear diffusion operator. The exact nature of the NDF operator is varied according to the desired feature characteristics, and a general form of such an operator is given as Eq. 3.1:

$$U_{(n+1)} = U_{(n)} + dU_{(n)} \quad (3.1)$$

$$dU_{(n)} = \nabla(\hat{D}_{(n)} \nabla U_{(n)}) dt$$

$$= \left|\begin{array}{c} \frac{\partial}{\partial x} \\ \frac{\partial}{\partial y} \end{array}\right| \cdot \left|\begin{array}{cc} b^{xx}_{(n)} & b^{xy}_{(n)} \\ b^{yx}_{(n)} & b^{yy}_{(n)} \end{array}\right| \cdot \left|\frac{\partial}{\partial x} \frac{\partial}{\partial y}\right| \cdot U_{(n)} \cdot dt$$

where $U=U(x,y)$ is the coordinate-dependent image intensity, $\hat{D}_{(n)}$ is diffusivity tensor (with components $b^{xx}_{(n)}$, $b^{xy}_{(n)}$, $b^{yx}_{(n)}$, $b^{yy}_{(n)}$), and dt is the "time step" parameter, which controls the rate of image evolution. Subscript index denotes the iteration number of NDF process.

In preferred aspects, the present invention incorporates one or more of three known methods for NDF, as disclosed in Weickert 1997.

Scalar "Gradient Modulus"-driven Diffusion (SGMD)
Anisotropic Edge Enhancing Diffusion (AEED)
Anisotropic Coherence Enhancing Diffusion (ACED)

The input image is the gray scale reference image. 3.1 is applied with a diffusivity tensor as specified in SGMD, AEED, or ACED. This process may be iterated any number of times. The selection of SGMD, AEED, or ACED is performed on the basis of the morphology of the features being accentuated or suppressed.

In a preferred aspect, SGMD and/or AEED are used with features in which edge preservation is important. ACED is used with fiber-like details. If both fiber and edge preservation are required, all three methods may be used.

If isolated intensity peaks must be preserved, the present invention applies an additional transformation which we term Scalar Peak Enhancing Diffusion (SPED).

It is an advantage of the SPED process of the present invention that NDF may be optimized for isolated intensity peaks, for example those associated with granular material inside of cells. In performing a SPED iteration, the output of a SGMD iteration is convolved with a peak-shaped mask, in which pixel gray level values decay exponentially with distance from the mask center. The size of mask is pre-set to match the characteristic size of the peak-like image details which are to be accentuated. This procedure is iterated for some pre-set number of iterations and emphasizes sharp intensity peaks while suppressing noise.

Process 4) Thresholding by Optimal Histogram Bipartition

Preferably, the invention applies an optimal histogram bipartition (OHB) step for segmentation. It is a feature of the OHB method that it accommodates the broad dynamic range present in biological images.

The input of the OHB procedure is a grayscale image, optionally processed using steps 1-3 above. The output is a binary image, in which segmented pixels correspond to cellular features of interest.

Various OHB methods are known (e.g. Parker 1997, Paulus 1995) and there is a potential for bias in threshold selection arising from use of one or another of the OHB methods. Therefore, it is an advantage of the present invention that it calculates a threshold using some property (e.g. the mean of all four, the mean of the middle two values sorted in ascending order, the smallest or largest) of several thresholds calculated by multiple OHB methods. This statistical threshold value is less likely to suffer from bias introduced by any one of the OHB methods.

In a preferred aspect, four OHB methods are used to generate a threshold value:

The gray level value maximizing the entropy measure for binarization (Paulus 1995, pp. 278-281).

The gray level value maximizing the mean square separation measure for binarization (Paulus 1995, pp. 278-281).

The gray level value minimizing the Shannon measure of the image taken as a fuzzy set (Parker 1997, p. 125).

The gray level value minimizing the Yager measure of the image taken as a fuzzy set (Parker 1997, p. 125).

Process 5) Seeded Region Growing

The input to region growing is a grayscale reference image, and a binary image, which is created from the reference image by a process such as is described in Step 4. It is a disadvantage of the initial binary image that the binary pixels which represent features of interest in the reference image do not correspond exactly to those features in the reference image. Therefore, region growing is used so that a final binary image can better represent features in the reference image. It is an aspect of the present invention that a seeded region growing method uses the initial binary image as its seed image. A tunable iterative procedure (e.g. as described in Russ, 1991, pp. 87-89) is then used to add binary pixels to regions. Tuning is defined as using the statistical properties of the growing objects, their vicinities and the background to select candidate pixels, with one embodiment shown in equation 5.1. The statistical parameters are recalculated iteratively, and the procedure is continued until optimal assignment of pixels to regions of interest is obtained.

$$T_N = \max(\text{Mean}[U|B_N] + k_B \cdot \text{Std}[U|B_N], \text{Mean}[U|Bck_N] + k_{Bck} \cdot \text{Std}[U|Bck_N])), \quad (5.1)$$

where $T_N$ is the threshold used for the current iteration, Mean$[U|B_N]$ and Std$[U|B_N]$ are mean and standard deviation calculated by the ensemble of boundary pixels, Mean$[U|Bck_N]$ and Std$[U|Bck_N]$ are mean and standard deviation calculated by the ensemble of background pixels (i.e. pixels not included in the object $O_N$ or in the boundary $B_N$), and $k_B$ and $k_{Bck}$ are controlling coefficients with values close to unity.

At the N-th iteration of the region growing process, a candidate boundary pixel $p(p \subset B_N)$, adjacent to the growing set of pixels $O_N$ (at first iteration, $O_1$ coincides with the seed image) is included in the growing set of pixels $O_{N+1}$ for the next iteration, if and only if the corresponding gray value $U(p)$ on the reference image U exceeds the threshold value of $T_N$. This threshold is calculated from global statistics of the image U as in Eq. X.

The iterative process continues until there is no candidate pixel (as defined by $U(p) > T_N$) adjacent to the growing set of pixels.

Process 6) Texture Transform

It is an advantage of the invention that segmentation and analysis of unstained or vitally stained specimens is possible. Such specimens are acquired using differential interference contrast (DIC), brightfield, or other forms of nonfluorescence microscopy. These methods are most useful in imaging living cells which are intolerant of fluorescence or other staining procedures.

In a key aspect, the present invention localizes intensity undulations of defined textural types, to enhance the detectability of features. The texture transform procedures are based upon gray level co-occurrence statistics (e.g. as disclosed in Parker 1997, p. 155). These procedures take as their input gray level reference images and create as their output gray level processed images in which features of appropriate texture are brighter than other features (are enhanced). Said enhanced features can then be segmented using procedures similar to those used for fluorescent images. Thus, it is a key advantage of the texture transform that a similar set of segmentation procedures may be used to analyze fluorescent and nonfluorescent materials.

In a preferred aspect, an "energy" texture transform (as described in Parker 1997, p. 160) is used. This transform is parameterized by the value of minimal morphological scale (MMS) of the specimen. The MMS is user-defined as a minimal size for meaningful image detail.

While texture transforms are preferred methods for enhancing nonfluorescent images prior to segmentation, it is to be appreciated that other transforms could be used. The key aspect is an enhancement in which an intensity increase in the output image is dependent upon structural characteristics of features in a reference image.

Process 7) Morphological Refinement of Detected Features

Fine projections, various sizes of holes or other discontinuities in feature boundaries can cause an undesirable variability in segmented shapes. In turn, this could lead to degraded performance of quantification algorithms. For example, skeletonization algorithms function poorly with jagged object edges. It is a feature of the present invention that morphological smoothing and sieve-by-size controlled hole filling are used prior to quantification. The value of MMS serves as a threshold size for a smoothing procedure. In a preferred aspect, this procedure removes all image details of size less than the MMS, thereby removing roughness.

Process 8) Quantification by Local Contrast

Generally, features are defined by their intensity relative to the intensity of surrounding cellular material. The local contrast between a feature and its local surround is defined in eq. 8.1.

$$\text{Local contrast} = \text{Mean}[U|\text{Feature}]/\text{Mean}[U|\text{Feature surround}] \quad (8.1)$$

The contrast value may be calculated directly from the reference image, or from locations defined on a processed image and transferred to a reference image.

Process 9) Distributional Feature Analyses

The distribution of a feature upon some measured characteristic can reflect underlying biology. It is common to see frequency histograms of feature size or intensity used to reflect underlying biology.

The present invention uses mixed feature distributions as indices of changes in a cell sample. The feature distribution is modeled by a probability density distribution function (PDDF). Then, hypotheses are tested against some predetermined model of what the frequency distribution should be. A unimodal distribution would result if, for example, cell granules were distributed about a single characteristic size. A bimodal distribution would result if cell granules are so altered by treatment that a population of larger or smaller granules appears (as with the Transfluor assay from Norak). In this case, a judgment that a particular treatment is effective may be made on the basis of extent to which an observed PDDF is bimodal.

In the specific case of a bimodal distribution of feature x, the mixed PDDF $P_{mix}(x)$ is expressed in terms of discrete PDDFs of its two components as shown in expression 9.1:

$$P_{mix}(x) = \alpha P_1(x) + (1-\alpha) P_2(x), \quad 0 \leq \alpha \leq 1 \tag{9.1}$$

where both partial PDDFs $P_1(x)$, $P_2(x)$ have finite averages and dispersions $\mu_i$ and $\sigma_i$ (i=1, 2). In the bimodal representation of the mixed PDDF (9.1), $\alpha$ is a weighting parameter for a bimodal model. The two weighting factors $\alpha$ and $(1-\alpha)$ reflect the relative amounts of contribution of the partial PDDFs $P_1(x)$, $P_2(x)$ to the mixed PDDF $P_{mix}(x)$.

The mean and the dispersion of the mixed PDDF shown in (9.1) are:

$$\mu_{mix} = \alpha\mu_1 + (1-\alpha)\mu_2 \tag{9.2a}$$

$$\sigma_{mix}^2 = \alpha\sigma_1^2 + (1-\alpha)\sigma_2^2 + \alpha(1-\alpha)(\mu_1-\mu_2)^2 \tag{9.2b}$$

where $\mu_{mix}$, and $\sigma_{mix}$ are the mean and standard deviation of the mixed sample, respectively. An experimental estimate $\overline{\alpha}$ of the weighting parameter $\alpha$ may be calculated from a sample according to expressions (9.2a) and/or (9.2b), as shown in 9.3a and 9.3b.

$$\overline{\alpha} = \frac{\overline{\mu}_{mix} - \overline{\mu}_2}{\overline{\mu}_1 - \overline{\mu}_2} \tag{9.3a}$$

$$\overline{\alpha}_{1,2} = \frac{(1-B-C) \pm \sqrt{(1-B-C)^2 - 4(A-C)}}{2},$$

where $$A = \frac{\overline{\sigma}_{mix}^2}{(\mu_1 - \mu_2)^2}, \tag{9.3b}$$

$$B = \frac{\sigma_1^2}{(\mu_1 - \mu_2)^2},$$

$$C = \frac{\sigma_2^2}{(\mu_1 - \mu_2)^2}$$

Where estimates $\overline{\mu}_1$, $\overline{\mu}_2$, $\overline{\sigma}_1$, $\overline{\sigma}_2$, $\overline{\mu}_{mix}$, $\overline{\sigma}_{mix}$ are means and standard deviations of the partial samples and mixed sample. To define the partial samples, the mixed sample must be split. This is achieved by a threshold bipartition operation. The bipartition threshold t may be defined by any known method (e.g. the OHB method of Process 4).

In a preferred aspect, separation of the samples is expressed as a normalized distance between the means of the two populations, calculated as in expression 9.4.

$$SS = |\overline{\mu}_1 - \overline{\mu}_2| / \sqrt{\overline{\sigma}_1^2 + \overline{\sigma}_2^2} \tag{9.4}$$

where SS is sample separation.

In another preferred aspect, the proportion of the mixed distribution contributed by each partial distribution is $\overline{\alpha}$ as shown above.

SS and $\overline{\alpha}$ are preferred parameters for distribution feature analysis of the present method.

10) Frequency Domain Detection of Granular Details

Granular structures (e.g. vesicles) within the cell body can increase or decrease in size and intensity in ways that reflect biology. Therefore, it is a feature of the present invention that granular structure analyses may be made by analyzing the image energy spectrum. The energy spectrum is described by an analytical expression which evaluates both granular and nongranular features.

The general form of an energy spectrum is shown in eq. 10.1.

$$E(\rho) = \langle F(\rho,\psi) F^*(\rho,\psi) \rangle_\psi, \tag{10.1}$$

where $E(\rho)$ is the energy spectrum, $F(\rho, \psi)$ is Fourier transform of the original image expressed in polar coordinates, $\langle \ldots \rangle_\psi$ denotes averaging by an angular coordinate, and $\rho$ and $\psi$ are radial and angular coordinates in Fourier space, correspondingly.

Using known methods (e.g. Granlund et al., 1995), granules are treated as a set of scattered intensity peaks of approximately the same width. In a preferred aspect, the intensity profile of a granule is modeled by a Gaussian function (Eq. 10.2)

$$A(\vec{r}) \propto f(a) e^{-\frac{1}{2}\left(\frac{\vec{r}-\vec{r}_0}{a}\right)^2}, \tag{10.2}$$

where $a$ is the effective average radius of a granule, $\vec{r}_0$ is granule's location. $f(a)$ is a proportionality multiplier which relates the granule's brightness to its size ($f(a) \sim a^3$). With bright granules (e.g. fluorescence), proportionality multiplier $f(a)$ improves size measurements because a granule's brightness is proportional to its volume.

The energy spectrum of granules of the same size is defined as the square of modulus of Fourier transform of the Gaussian function (Eq. 10.3):

$$E_{granules}(\rho) \sim f(a) e^{-(a\rho)^2} \tag{10.3}$$

It is known (Granlund et al., 1995), that nongranular features yield power terms in an energy spectrum as shown in Eq. 10.4:

$$E_{nongranular}(\rho) \sim \rho^{-3} \tag{10.4}$$

A model expression (Eq. 10.5) for the energy spectrum is therefore taken in the form of weighted sum of contributions of the two main components—nongranules and granules:

$$E(\rho) = E_{nongranulars}(\rho) + E_{granules}(\rho) = A_1 \rho^{-3} + A_2 f(a) e^{-(a\rho)^2} \tag{10.5}$$

where $A_1$, $A_2$ are >0.

The discrimination between biological conditions is made on the basis of the two fitted parameters (obtained from Eq. 10.5)—a (an estimated mean granule radius) and ratio ($A_2/A_1$), which reflects the contribution of the granular component to the power spectrum.

The analysis proceeds through energy spectrum construction and then quantification.

Energy Spectrum Construction

The Fourier spectrum of granules is produced by known methods (as described in Press 1992, p. 689). This spectrum is then reduced to the discrete one-dimensional frequency dependence after averaging by an angle coordinate, and discretization of radial distance in Fourier space. This procedure implements conversion (10.1), defined for the discrete set of values of radial distance $\rho_j$ (j=1, ... $N_\rho$), where $N_\rho$ is the number of discrete values of radial distance. As a result of this operation, the average spectrum intensity $<E>_j$ is calculated for each value of $\rho_j$, producing the discrete representation of spectrum $\{\rho_j, <E>_j\}$.

Quantification (Spectrum Fitting)

Known methods of nonlinear fitting (Press 1992, p. 683, p. 408) are used to obtain three fitting parameters from the energy spectrum—a (effective average radius of granule) and amplitudes $A_2$ and $A_1$ from model expression (10.5). In a preferred aspect, the values of $\alpha$ and ratio ($A_2/A_1$) are used for image quantification.

11) Demarcation Mapping

Demarcation mapping is a procedure used to perform geometric analyses on segmented images. The present invention uses demarcation mapping to localize geometric areas around neurite origins (FIG. 10). Most typically, each cell has a demarcated region around it, output by the demarcation mapping process.

As one aspect of demarcation mapping, a segmented neurite image (as output from processes described below) is skeletonized (e.g. as disclosed in Russ 1991, pp. 483-485). In the skeletonized image, neurites, neurite end points, neurite branch points, and the cells of origin for each neurite on a corresponding cell image (attachment points) may be found.

A pixel of a binary skeleton is considered to be a branch point if and only if there are more than two non-zero pixels in its 3×3 neighborhood.

A pixel of a binary skeleton is considered to be a endpoint if and only if there is only one non-zero pixel in it's 3×3 neighborhood.

A pixel of a binary skeleton is assumed to be an attachment point of neurite to cell if it is an end point and is proximal to the cell.

A neurite is considered as originating in a specific cell body if that neurite lies within the demarcated region of a cell in the corresponding cell tessellation image.

As a second aspect of demarcation mapping, a cell tessellation image is created. Tessellation is the result of unconditional region growing or binary dilation of any segmented targets which serve as seeds (Parker 1997, p. 69). In the present case, the targets are most typically cell bodies.

Therefore, demarcation mapping has two input images. A segmented neurite image is input to skeletonization. A segmented cell image is input to tessellation. A skeletonized neurite image and a tessellated cell image are intermediate outputs. The final outputs are measurements of neurite geometry, taken from the skeletonized image, and localization of neurite origins to specific cells, taken from the tessellated cell image.

12) Background Correction

Background correction removes spatial nonuniformity in illumination or emission intensity from an original image. The preferred method is to process an image to create a highly smoothed image in which specimen detail is absent but low frequency background components remain. The highly smoothed image is subtracted from or divided into the original image.

Various procedures for smoothing images will be apparent to one skilled. For example, Gaussian smoothing, grayscale opening, pair-wise filtering (opening followed by closing or closing followed by opening), or alternating sequential filtering (Jahne 1999, p. 627-680) have all been used in this type of operation.

It is to be appreciated that a smoothing operation or other method of background correction may also be used to optimally select features of a given size, while de-emphasizing features which are bigger.

13) Sieving

Sieving is a process by which a binary image is filtered to remove segmented targets which have geometry that does not correspond to features of interest. For example, images are sieved by size and only features which fall within a specified size range are left in the sieved image. Many other types of sieve depend upon geometric properties of features. For example, images could be sieved by shape descriptors (as disclosed in Russ 1999, p. 553-555). It is a feature of the present invention that sieving is applied using single (e.g. size) or multiple criteria. As an example of multi-criteria sieves, the method of the present invention sieves two images according to different criteria (e.g. round in the first image and elongated in the second), and then performs a further pairwise sieving step. In pairwise sieving, only those features which meet another criterion (e.g. elongated objects proximal to round objects) are retained.

Method for Neurite Assays

Neurite material is structurally complex and images contain many potentially confusable features. It is a feature of the present method that it performs automated and accurate detection of neurites within a broad variety of specimens, including fluorescently labeled and unlabeled specimens.

In one aspect, the method uses an energy texture transform to improve subsequent segmentation in unstained images.

In another aspect, the method improves detectability of neurites and cell bodies by employing processes of nonlinear diffusion filtering, optimal histogram bipartition, seeded region growing, sieving, and morphological image refinement.

In another aspect, the method demarcates zones of influence for cell bodies, using a tessellation procedure. From these zones, neurite structures may be related to their cell bodies of origin. It is a feature of the present invention that a broad variety of neurite structures may be identified and related to cell bodies of origin.

Details of procedures for neurite analysis are best shown in FIGS. 3-10.

Method for Granular Translocation Assays

The present invention performs analyses of granular material as commonly observed in nuclear translocation assays such as the Transfluor assay from Norak Inc. In these assays, cytoplasmic granules of pre-defined size must be segmented and analyzed, while granular artifacts outside cytoplasm must be ignored. It is a feature of the present method that it detects even weakly labeled cytoplasmic material within which granules may then be localized.

In one aspect, the method improves detectability of granules and cytoplasm by employing processes of nonlinear suppression of high intensity peaks, nonlinear diffusion filtering or adaptive noise smoothing, optimal histogram bipartition, seeded region growing, and morphological image refinement.

In a preferred aspect the method uses distributional feature analysis to report alterations in granular intensity or geometric properties.

Details of procedures for granular translocation assays are shown in FIGS. 11-17.

Method for Nuclear Translocation Assays

Nuclear translocation is commonly quantified by a change in the relative intensity of fluorescent label contained in nuclei and cytoplasm. Typically, two images are acquired. One image best demonstrates the nuclei as a geometrical positioning aid and/or to show viability or other cell functional aspects. A second image best shows cytoplasm, with fluorescence intensity corresponding to the local concentration of the labeled molecule of interest.

In one aspect of the present invention, translocation is quantified from cell images processed to best show nuclear and cytoplasmic areas for making measurements. Preferably, processing to show nuclei includes nonlinear suppression of high intensity peaks, noise suppression by nonlinear diffusion filtering, background correction, optimal histogram bipartition, and morphological refinement. Preferably, processing to show cytoplasm includes nonlinear suppression of high intensity peaks, noise suppression by adaptive noise smoothing or nonlinear diffusion filtering, background correction, optimal histogram bipartition, and morphological refinement.

In one aspect, distributional feature analysis may be used to quantify translocation. In this case, the relative contributions of darker and brighter nuclei and/or cytoplasm may be distinguished from a bimodal character of the nuclear or cytoplasmic intensity histograms.

Any of the intensity parameters calculated from the intensity quantification process may be subjected to distributional analyses. For example, the nuclear-cytoplasmic ratio, the nuclear intensity, and the cytoplasmic intensity may all be used.

The method for analysis of nuclear translocation assays is shown in FIGS. 18-23.

Method for Membrane Ruffling Assays

Some translocation events are characterized by a regionalized distribution of label within non-punctuated regions of cytoplasm, which are morphologically distinct or ridge-shaped elaborations, here referred to as "ruffles". Ruffles are defined as intensity-discriminated features of a specified cross-sectional size. The method is similar to that used for nuclear translocation assays, with detailed refinements to better detect ruffle objects. It is a feature of the functions of the present invention that they are integrated into a method that provides automated discrimination of membrane ruffles (FIGS. 24-28).

Although preferred embodiments of the invention have been disclosed for illustrative purposes, those skilled in the art will appreciate that many additions, modifications and substitutions are possible without departing from the scope and spirit of the invention.

MATERIALS CITED

Anderson, C. M., Georgiou, G. N., Morrison, I. E. G., Stevenson, G. W. and Cherry, R. J. Tracking of cell surface receptors by fluorescence digital imaging microscopy using a charge-coupled device camera, *Journal of Cell Science* 101:415-425 (1992).

Benveniste, M., Schlessinger, J. and Kam, Z. Characterization of internalization and endosome formation of epidermal growth factor in transfected NIH-3T3 cells by computerized image-intensifed three-dimensional fluorescence microscopy, *The Journal of Cell Biology* 109: 2105-2115 (1989).

Chassery, J. M. and Garbay, C. An interative segmentation method based on a contextual color and shape criterion, *IEEE PAMI* 6:794 (1984).

Conway, B. R., Minor, L. K., Xu, J. Z., Gunnet, J. W., DeBiasio, R., D'Andrea, M. R., Rubin, R., DeBiasio, R., Giuliano, K., Zhou, L. and Demarest, K. T. Quantification of G-protein coupled receptor internalization using G-protein coupled receptor-green fluorescent protein conjugates with the ArrayScan high-content screening system. *Journal of Biomolecular Screening* 4:75-86 (1999).

Crissman, J. D., Visscher, D. W. and Kubus, J. Image cytophotometric DNA analysis of atypical hyperplasias and intraductal carcinomas of the breast, *Archives of Pathology and Laboratory Medicine* 114:1249-1253 (1990).

Dawes, E. A. Quantitative Problems in Biochemistry, Baltimore: Williams and Wilkins, pp. 293-311, 1972.

De Le Torre, C. and Navarrete, M. H. Experimental Cell Research 88: 171-174, 1974.

Deligdisch et al., Cancer 72:3253-3257, 1993.

Feynman R. et al, The Feynman Lectures on Physics, Addison-Wesley Publishing Co., Inc., Reading, Mass., Palo Alto, London, 1964, p. 35.

Freshney, R. I. Quantitation and Experimental Design, in Culture of Animal Cells, a Manual of Basic Technique, 2nd ed., New York: Alan R. Liss, pp. 227-256, 1987.

Fu K. S. and Mui, J. K. A Survey on Image Segmentation, *Pattern Recognition* 13:3-16 (1981).

Galbraith, W. Wagner, M. C. E., Chao, J., Abaza, M., Ernst, L. A., Nederlof, M. A., Hartsock, R. J., Taylor, D. L. and Waggoner, A. S. Imaging cytometry by multiparameter fluorescence, *Cytometry* 12:579-596 (1991).

Garbay, C. Image structure representation and processing: a discussion of some segmentation methods in cytology, *IEEE Transactions PAMI* 2:140 (1986).

Georget, V., Térouanne, B., Lumbroso, S., Nicolas, J.-C. and Sultan, S. Trafficking of Androgen Receptor Mutants Fused to Green Fluorescent Protein: A New Investigation of Partial Androgen Insensitivity Syndrome, *The Journal of Clinical Endocrinology & Metabolism* 83:3597-3603 (1998).

Gibson, D. and Gaydecki, P. A. The application of local gray level histograms to arganelle classification in histological images, Gibson, D. and Gaydeicki, P. A. *Computers in Biology and Medicine* 26:329-337 (1996).

Gil, J., Marchevsky, A. M. and Sialge, D. A. Applications of computerized interactive morphometry in pathology: I. Tracings and generation of graphics standards, *Laboratory Investigation* 54:222-227 (1986).

Giroud, F. *Biology of the Cell* 44:177-188 (1982)

Granlund G. H., Knutsson H., Signal Processing For Computer Vision, Kluwer Academic Publishers, 1995, pp 174-176.

Hueckel, M. H. An operator which locates edges in digitized pictures, *Journal of the Association of Computing Machines* 1:113 (1971).

Ishido, T., Itabashi, M., Ochiai, A., Hirota, T., Yokota, T. and Saito, D. Morphometric analysis of colorectal dysplasia with image processing, *Archives of Pathology and Laboratory Medicine* 118:619-623 (1994).

Kawamoto, H., Koizumi, H. and Uchikoshi, T. Expression of the G2-M checkpoint regulators cyclin B1 and cdc2 in nonmalignant and malignant human breast lesions, American Journal of Pathology 150:15-23 (1997).

Lee et al., A processing strategy for automated Papanicolaou smear screening, *Analytical and Quantitatiave Cytology and Histology* 14:415-425 (1992).

Lockett, S. J., Jacobsen, K., O'Rand, M., Kaufman, D. G., Corcoran, M., Simonsen, M. G., Taylor, H. and Herman, B. Automated image-based cytometry with fluorescence-stained specimens, *Biotechniques* 10:514-519 (1991).

Luby-Phelps, K., Lanni, F. and Taylor, D. L. Behavior of a fluorescent analogue of calmodulin in living 3T3 cells, *The Journal of Cell Biology* 101:1245-1256 (1985).

Macaulay, C. and Palcic, B. A comparison of some quick and simple threshold selection methods for stained cells, *Analytical and Quantitative Cytology and Histology*, 3:134 (1988).

Macaulay, C. and Palcic, B. An edge relocation segmentation algorithm, *Analytical and Quantitative Cytology and Histology*, 6:394 (1990).

Malay, F.-E., Vittoz, M., Urwyler, A., Koshikawa, K., Schleinkofer, L. and De Weck, A. L. A dual microtiter plate (192 sample) luminometer employing computer-aided single-photon imaging applicable to cellular luminescence and luminescence immunoassay, *Journal of Immunological Methods* 122:91-96 (1989).

Martin, H., Voss, K., Hufnagel, P. and Frolich, K. Automated image analysis of gliomas: An objective and reproducible method for tumor grading, *Acta Neuropathologica* 63:160-169 (1984).

Miraglia, S., Swartzman, E. A., Mellentin-Michelotti, J., Evangelista, L., Smith, C., Gunawan, I., Lohman, K., Goldberg, E. M., Manian, B. and Pau-Miau, Y. Homogeneous cell- and bead-based assays for high-throughput screening using fluorometric microvolume assay technology. *Journal of Biomolecular Screening* 4:193-204 (1999).

Mize, R. R., Holdefer, R. N. and Nabors, L. B. Quantitative immunocytochemistry using an image analyzer. I. Hardware evaluation, image processing, and data analysis, *Journal of Neuroscience Methods* 26:1-24 (1988).

Morrison, I. E. G., Anderson, C. M., Georgiou, G. N., Stevenson, G. V. W. and Cherry, R. J. Analysis of receptor clustering on cell surfaces by imaging fluorescent particles, *Biophysical Journal* 67:1280-1290 (1994).

O'Gorman, L., Sanderson, A. C. and Preston, K. Jr. A system for automated liver tissue image analysis: methods and results, *IEEE Transactions BME* 9:696 (1985).

Oldmixon, E. H., Butler, J. P. and Hoppin, F. G. Semi-automated measurement of true chord length distributions and moments by video microscopy and image analysis, *Journal of Microscopy* 175:60-69 (1994).

Omalley, D. M. Calcium permeability of the neuronal nuclear envelope: evaluation using confocal volumes and intracellular perfusion, *Journal of Neuroscience* 14:5741-5758 (1994).

Ong, S. H., Giam, S. T., Jayasooriah, Sinniah, R. Adaptive window-based tracking for the detection of membrane structures in kidney electron micrographs, *Machine Vision and Applications* 6:215 (1993).

Parker, J. R., Algorithms for Image Processing and Computer Vision, John Wiley & Sons, 1997

Paulus, D. W. R., Hornegger J., Pattern Recognition and Image Processing in C++, Vieweg 1995

Press W. H. et all, Numerical Recipes in C, Cambridge University Press, 1992

Proffit et al., *Cytometry* 24:204-213, 1996

Ramm, P. Imaging systems in assay screening, *Drug Discovery Today* 4:401-410 (1999).

Ramm, P., Soltys, B., Cholewinski, A., Nadon, R., Alexandrov, Y., Cybuch, J., Donders, P., Kennedy, A. and Bula, W. Automated screening of neurite outgrowth, Paper presented at the 2001 Annual Meeting of the Society for Biomolecular Screening, September 2001.

Ramm, P., Soltys, B., Cholewinski, A., Nadon, R., Alexandrov, Y., Cybuch, J., Donders, P., Kennedy, A. and Bula, W. Automated screening of neurite outgrowth, Submitted to Journal of Biomolecular Screening, January 2002.

Refenes, A. N., Jain, N. and Alsulaiman, M. M. An integrated neural network system for histological image understanding, *Proceedings of the SPIE Machine Vision Systems Integration in Industry* 1386:62 (1990).

Russ, J. C., Computer Assisted Microscopy, Plenum Press, 1991, pp. 87-89.

Russ, J. C., Image Processing Handbook, CRC Press LLC, 1999

Santisteban, M.-S., Montmasson, M.-P., Giroud, F., Ronot, X. and Brugal, G. Fluorescence image cytometry of nuclear DNA content versus chromatin pattern: A comparative study of ten fluorochromes, *The Journal of Histochemistry and Cytochemistry* 40:1789-1797 (1992).

Sawicki, W., Rowinski, J. and Swenson, R. *Journal of Cell Physiology* 84:423-428, (1974).

Serra, J. Image Analysis and Mathematical Morphology, Acadmic Press, 1982.

Smeulders, A. W. M., Veldstra, L. L., Ploem, J. S. and Cornelisse, C. J. Texture analysis of cervical cell nuclei by segmentation of chromatin patterns, *Journal of Histochemistry and Cytochemistry* 1:199 (1979).

Smith, T. G., Marks, W. B., Lange, G. D., Sheriff, W. H. and Neale, E. A. A fractal analysis of cell images, *Journal of Neuroscience Methods* 27:173-180 (1989).

Schroeder, K. S. and Neagle, B. D. FLIPR:; A new instrument for accurate, high throughput optical screening, *Journal of Biomolecular Screening* 1:75-84 (1996).

Seniuk, N. A., Tatton, W. G., Cannon, P. D., Garber, A. T. and Dixon, G. H. First expression of protamine message in trout testis, *Annals of the New York Academy of Sciences* 637:277-288 (1991).

Souchier, C., Ffrench, M., Benchaib, M., Catallo, R. and Bryon, P. A. Methods for cell proliferation analysis by fluorescent image cytometry, *Cytometry* 20:203-209 (1995).

Stotzka, R., Manner, R., Bartels, R. H. and Thompson, D. A hybrid neural and statistical classifier system for histopathologic grading of prostatic lesions, *Analytical and Quantitative Histology and Cytology* 17:204-218 (1995).

Takamatsu, T. et al., Acta Histochem. Cytochem. 19: 61-71, 1986

Taylor, D. L., Woo, E. S. and Giuliano, K. A. Real-time molecular and cellular analysis: the new frontier of drug discovery, *Current Opinion in Biotechnology* 12:75-81 (2001).

Thompson, D., Bartels, H. G., Haddad, J. W. and Bartels, P. H. Scene segmentation in a machine vision system for histopathology, *SPIE Proceedings New Technologies in Cytometry and Molecular Biology* 1206:40 (1990).

Wied, G. L. et al. Expert systems as classifiers in diagnostic cytopathology, *IEEE/Ninth Annual Conference of the Engineering in Medicine and Biology Society*, pp. 1915-1917 (1987).

Zoli, M., Zini, I., Agnati, L. F., Guidolin, D., Ferraguti, F. and Fuxe, K. *Neurochemistry International* 16:383-418 (1990).

Wolberg, W. H., Street, W. N. and Mangasarian, O. L. Breast cytology diagnosis with digital image analysis, *Analytical and Quantitative Cytology and Histology* 15:396-404 (1993).

What is claimed:

1. An automated control process for analyzing the translocation of material between nongranular subcellular compartments comprising the steps:
   acquiring a first image of a cellular material sample providing geometric information of at least one subcellular compartment;
   acquiring a second image of the cellular material sample providing information of at least one labeled molecule of interest, with label intensity corresponding to the local concentration of the labeled molecule;
   wherein each image is processed by the following steps:
      preprocessing;
      binarization;
      region growing;
      morphological refinement;
      sieving;
   and wherein the label intensity in the second image is quantified based on the geometric information of at least one subcellular compartment from the first image, using the processed images.

2. The automated control process of claim 1, wherein at least one subcellular compartment is a cell nucleus.

3. The automated control process of claim 1, wherein the step of preprocessing comprises the algorithmic processes:
   nonlinear suppression of high intensity peaks;
   optional noise smoothing by:
      adaptive noise smoothing (Gaussian); or
      adaptive noise smoothing and feature enhancement by nonlinear diffusion filtering;
   and
   optional background correction.

4. The automated control process of claim 1, wherein the step of binarization comprises an algorithmic process of:
   thresholding by optimal histogram bipartition.

5. The automated control process of claim 1, wherein the step of quantification comprises at least one of the algorithmic processes:
   quantification by local contrast; and
   distributional feature analyses.

6. A computer program stored on a computer readable medium arranged to perform the automated control process of claim 1 when executed on a computer.

7. An optomechanical system for automated analysis of cellular elaboration, comprising:
   an electronic camera;
   an optical subsystem providing a focused image for the camera;
   a positioning subsystem positioning specimens in a plurality of containers at a location within the range of the optical subsystem;
   a computer controlling the camera and the subsystems, the computer running a computer program, on a computer-readable medium, being arranged to perform an automated control process for analyzing the translocation of material between nongranular subcellular compartments comprising the steps:
      acquiring a first image of a cellular material sample providing geometric information of at least one subcellular compartment;
      acquiring a second image of the cellular material sample providing information of at least one labeled molecule of interest, with label intensity corresponding to the local concentration of the labeled molecule;
      wherein each image is processed by the following steps:
         preprocessing;
         binarization;
         region growing;
         morphological refinement;
         sieving;
      and wherein the label intensity in the second image is quantified based on the geometric information of at least one subcellular compartment from the first image, using the processed images.

8. The system of claim 7, further comprising an interface to laboratory equipment.

* * * * *